US008285666B2

(12) United States Patent
Wegner et al.

(10) Patent No.: US 8,285,666 B2
(45) Date of Patent: Oct. 9, 2012

(54) PHENOTYPE PREDICTION METHOD

(75) Inventors: Jörg Kurt Wegner, Mechelen (BE);
Herman Van Vlijmen, Mechelen (BE);
Carlo Willy Maurice Boutton,
Wielsbeke (BE)

(73) Assignee: Tibotec Pharmaceuticals Ltd, Little Island, County Cork (IE)

( * ) Notice: Subject to any disclaimer, the term of this patent is extended or adjusted under 35 U.S.C. 154(b) by 713 days.

(21) Appl. No.: 12/515,091

(22) PCT Filed: Nov. 30, 2007

(86) PCT No.: PCT/EP2007/063047
§ 371 (c)(1),
(2), (4) Date: May 15, 2009

(87) PCT Pub. No.: WO2008/065180
PCT Pub. Date: Jun. 5, 2008

(65) Prior Publication Data
US 2010/0049689 A1 Feb. 25, 2010

(30) Foreign Application Priority Data
Nov. 30, 2006 (EP) .................................... 06125160

(51) Int. Cl.
*G06F 17/00* (2006.01)
*G06N 7/04* (2006.01)
(52) U.S. Cl. ......................................................... 706/54
(58) Field of Classification Search .................. None
See application file for complete search history.

(56) References Cited

U.S. PATENT DOCUMENTS 7,640,113 B2 * 12/2009 Frudakis et al. ................ 702/19
2003/0158672 A1    8/2003 Ramnarayan et al.
2003/0215877 A1   11/2003 Love et al.

OTHER PUBLICATIONS

Boutton, Carlo W. et al. "Genotype Dependent QSAR for HIV-1 Protease Inhibition". Journal of Medicinal Chemistry, vol. 48, No. 6, Mar. 2005, pp. 2115-2120, XP002433943.

* cited by examiner

*Primary Examiner* — Omar Fernandez Rivas
*Assistant Examiner* — Luis Sitiriche
(74) *Attorney, Agent, or Firm* — Woodcock Washburn LLP

(57) ABSTRACT

The present invention relates to methods and systems for predicting the phenotype conferred by a protein. Such methods and systems facilitate the design, optimization, and assessment of the efficiency of a therapeutic regimen based on the genotype of the disease affecting the patient.

22 Claims, 19 Drawing Sheets

PHENOTYPE PREDICTION METHOD

CROSS REFERENCE TO RELATED APPLICATIONS

This application is the national stage of PCT Application No. PCT/EP2007/063047 filed Nov. 30, 2007, which claims priority from European Patent Application No. 06125160.9, filed Nov. 30, 2006, the entire disclosures of which are hereby incorporated in their entirety.

The present invention relates to methods and systems for predicting the phenotype conferred by a protein.

In particular, such methods and systems facilitate the design, optimisation, and assessment of the efficiency of a therapeutic regimen based on the genotype of the disease affecting the patient.

An area in which it is advantageous to be able to predict the phenotype conferred by a particular protein is in the field of drug resistance. It is becoming increasingly apparent that various pathogens are developing drug resistance. This has the effect that previously used therapeutic agents cease to be effective in treating the disease.

One area where this is particularly apparent is in relation to the human immunodeficiency virus (HIV), which is a retrovirus.

Previously patients could successfully be treated by administering various different anti-HIV-1 agents alone as a monotherapy. However, over time it was found that the effectiveness of such agents decreased. Research has demonstrated that one of the main reasons for the observed decrease in effectiveness is the development of resistance of the virus to the drugs used. This is largely due to the ability of HIV to continuously generate a number of genetic variants in a replicating viral population. These genetic changes generally alter the configuration of the HIV reverse transcriptase (RT) and protease (PR) molecules in such a way that they are no longer susceptible to inhibition by the compounds developed to target them. If antiretroviral therapy is ongoing and if viral replication is not totally suppressed, over time, the selection of genetic variants is inevitable and the viral population becomes resistant to the drug.

Dual and triple therapy has since been used in an attempt to maintain the effectiveness of the treatment. However, it has been found that, while it may be postponed, treatment failure eventually occurs.

As a result of the fact that patients in the developed world are prescribed a cocktail of different drugs, it is not always the case that the initial infection originates from the wild type; rather a patient may be infected with a drug resistant strain which will inevitably lead to drug resistance. Where a patient is infected with a drug resistant strain, the treatment options are immediately reduced. The development of an effective initial therapy for such patients is clearly of importance and in order to do this, information regarding the drug resistance of the strain with which the patient is infected is required.

At present there are a large number of possible drug combinations and combination therapies which make it very difficult, if not impossible, for a physician accurately to predict the optimal combination for a given individual. Selecting an ineffective initial combination can lead to the patient experiencing a rapid clinical progression or deterioration. The key to developing a tailored, individualised therapy lies in the effective profiling of the patient's viral population in terms of resistance to available drugs.

There are various solutions to this problem which are currently used.

Phenotyping directly measures the sensitivity of a patient's pathogen or malignant cell to particular therapeutic agents. This process can be slow, labour intensive and, consequently, expensive.

Genotyping tests identify specific mutations in the viral genome which lead to amino acid changes in one of the viral proteins, known or suspected to be associated with resistance. Genotyping tests can be performed rapidly but there is a problem with the fact that there are a large number of individual mutations which are linked to drug resistance in some way and more mutations are constantly being discovered. Furthermore, drug development continues in parallel. The relationship between a given mutation (insertion, deletion or point mutation) and drug resistance is very complex.

It has become increasingly evident that the influence of a certain mutation in HIV protease on drug resistance cannot be considered independently of other mutations. For example, it is clear that one mutation may have an unexpected antagonistic or synergistic effect on another. Attempts have been made to overcome this problem to predict in silico the phenotypic behaviour of HIV-1 protease mutants. Such methods are based on statistical techniques and use, for example, algorithms, neural networks, support vector machines, cluster analysis, decision trees or linear discriminant analysis. A disadvantage of such methods is that they are retrospective in nature and have to be updated whenever a new mutational pattern or antiviral drug is identified. An example of such a technique is described in WO2004/111907 wherein a method for quantitating the individual contribution of a mutation or combination of mutations to the drug resistance phenotype exhibited by HIV is described. The method involves performing a linear regression analysis using data from a dataset of matching genotypes and phenotypes. The log fold resistance of the HIV is modelled.

The focus has moved from such techniques to the development of structure-based computational technologies. For example, Boutton et al, *J. Med Chem.* 2005, 48, 2115-2120 describe a structure-based computational method quantitatively to predict the resistance or sensitivity of an HIV-1 protease strain toward amprenavir. The X-ray structure of HIV-1 protease complexed with amprenavir is generated as a template for the generation of a large number of homology models. The interaction energy between the HIV-1 protease and the drug at the level of the residue is then calculated and includes a consideration of coulomb, van der Waals and hydrogen-bond interactions of each residue with the drug. This technique represents an improvement on previously used techniques on the basis that it accounts for the asymmetry of the HIV-1 protease dimer. However, even by the use of such a model, it is still the case that mutations which contribute to drug resistance may be overlooked.

The aim of the present invention is therefore to provide improved methods for interpretation of genotypic results to allow predictions of phenotype.

It is a further aim of this invention to provide methods for predicting the resistance of a protein of a particular genotype to a therapy or therapeutic agent.

It is a further aim of the invention to predict resistance of a patient to therapy.

It is also an aim of the invention to identify novel mutations in a protein that are associated with a change in the phenotype conferred by that particular protein.

The present invention solves these problems by providing a structure-based computational method wherein the contribution of a mutated residue or set of mutated residues to the phenotype conferred by a protein can be predicted. The method involves considering the interaction of the mutated protein with a partner molecule not just at the residue level as analysed conventionally but also at a holistic level of complex structure According to a first aspect of the present invention, there is provided a method of predicting the individual contribution of a mutated residue or set of mutated residues in a protein to the phenotype conferred by that mutated protein, said method comprising the steps of:
(a) generating a 3D model of a complex of a partner molecule bound to said mutated protein by comparison with a 3D model of a complex of the same partner molecule bound to at least one first reference protein;
(b) calculating the contribution of the mutated residue to the phenotype conferred by the mutated protein by quantifying the interaction energy between at least two of either (i) the protein and the partner molecule, (ii) the individual protein chains and the partner molecule, (iii) the individual protein residues and the partner molecule, (iv) the protein and the mutated residue, and (v) the individual protein chain(s) and the mutated residue;
(c) comparing all or a subset of the contributions calculated in step (b) with the equivalent contribution in the at least one first reference protein complex; and
(d) predicting the phenotype conferred by the mutated protein from the difference in said contributions.

Accordingly, the present invention provides an improved method by which it is possible to predict the phenotype that will be conferred by a particular mutated protein when interacting with a particular partner molecule. Examples of phenotypes which the method of the present invention may be used to predict include, but are not limited to, drug resistance, enzyme activity, binding affinity, DNA binding affinity, drug binding affinity, RNA binding affinity, antibody binding affinity, protein stability and virus viability. As noted above, the method of the present invention is of particular value where the partner molecule is a drug and the method is used to predict the drug resistance phenotype conferred by the mutated protein.

The mutated protein of the method of the present invention may be any protein of interest, for example, an enzyme, a structural protein, an antibody, a fragment of any one of these protein types and so on. In a preferred embodiment of the present invention, the mutated protein is a viral enzyme such as an HIV protein, particularly an HIV protease.

The term "partner molecule" as used herein is intended to refer to any entity which may interact with the protein to form a complex. Examples of partner molecules are substrates for a particular enzyme, co-factors for an enzyme, drug molecules, DNA or RNA molecules, transcription factors and other proteins. Where the mutated protein is an HIV protease, the partner molecule is preferably an anti-HIV drug.

The first step in the method of the present invention is to generate a 3D model of the partner molecule bound to the mutated protein in question. The 3D model of the complex should be generated using computer-implemented techniques. Examples of suitable techniques include but are not limited to single residue mutation and creation of side chain orientation by using a rotamer library; single residue mutation and creation of side-chain confirmation by sampling angles of this side chain followed by energy minimisation; single residue mutation and sampling angles of this and surrounding residues followed by an energy minimisation step; performing the afore-mentioned steps for multiple mutated residues in sequential order followed by a global energy minimisation step; performing the first three afore-mentioned techniques for multiple residues and an iterative process with a global energy minimisation between local optimisation steps e.g. single residue rotation; and homology modelling for a series of residues or the whole protein with or without allowing for different residue constraints. Such methods generally result in the generation of a 3D structure which is translated into conventional flat file format used in the Protein DataBase (PDB).

In order to assess the difference between this 3D model and a reference model, a comparison is made with the 3D model of the same partner molecule bound to a reference protein. The reference protein may, for example, be the wild type protein or a mutated version of the protein for which the phenotype is already known.

It may be the case that a 3D model of the partner molecule bound to a reference protein is already available from accessible databases such as the PDB. In this situation, there is no need to generate it again from first principles. However, if it is not available, it will be necessary to generate the 3D model of the complex of the partner molecule bound to the at least one reference protein. Advantageously this may be done by use of the three dimensional coordinates of the complex formed. Preferably, the three dimensional coordinates are determined by experiment eg from X-Ray diffraction data. However, a theoretical homology or NMR model may be used.

Having ascertained the experimental or theoretical three dimensional coordinates, the model is generally processed further to facilitate in silico processing, including steps such as building missing residues, adding hydrogen atoms, retaining bound solvent molecules, correcting protonation states and running short energy minimisations for correcting steric and electronically unfavourable atom and bond. Where a number of conformations for a particular residue are available, it is normal to select the conformation of lowest energy.

The 3D model of the complex of the partner molecule and the at least one mutated protein is preferably formed by homology modelling by comparison with the 3D model of a complex of the partner molecule bound to a first reference protein. In principle, however, this model could be generated from first principles.

As a first step it is necessary to identify the mutated residue or set of mutated residues in the mutated protein. Normally this will be experimentally derived e.g. from a sample obtained from a patient. The genetic sequence of a mutated protein may be evaluated by a number of suitable techniques, as will be clear to those skilled in the art. Most suitable are those techniques which allow for specific nucleic acid amplification, such as polymerase chain reaction (PCR) although other techniques, such as restriction fragment length polymorphism (RFLP) analysis will be equally applicable.

The mutation pattern can then be identified either by classical nucleic acid sequencing protocols e.g. extension termination protocols (Sanger technique; see Sanger F., Nicher, Coulson A Proc. Nat. Acad. Sci. 1977, 74, 5463-5467) or chain cleavage protocols. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer). Particular sequencing methodologies have been developed further by companies such as Visible Genetics.

Any of the novel approaches developed for unravelling the sequence of a target nucleic acid, either now or in the future will be perfectly applicable to the analysis of sequence in the present invention, including but not limited to mass spectrometry, MALDI-TOF (matrix assisted laser desorption ionization time of flight spectroscopy, (see Graber J, Smith C., Cantor C. Genet. Anal. 1999, 14, 215-219) chip analysis (hybridization based techniques) (Fodor S P; Rava R P; Huang X C; Pease A C; Holmes C P; Adams C L Nature 1993, 364, 555-6). It should be appreciated that nucleic acid sequencing covers both DNA and RNA sequencing.

Once the genetic sequence of the mutated protein is known, the pattern of mutation must be identified in the sequence. The term "mutation" as this is used herein, encompasses both genetic and epigenetic mutations of the genetic sequence of wild type protein. A genetic mutation includes, but is not limited to, (i) base substitutions: single nucleotide polymorphisms, transitions, transversions, substitutions and (ii) frame shift mutations: insertions, repeats and deletions. Epigenetic mutations include, but are not limited to, alterations of nucleic acids, e.g., methylation of nucleic acids. One example includes (changes in) methylation of cytosine residues in the whole or only part of the genetic sequence. In the present invention, mutations will generally be considered at the level of the amino acid sequence, and comprise, but are not limited to, substitutions, deletions or insertions of amino acids.

The "control sequence" or "wild type" is the reference sequence from which the existence of mutations is calculated. For example, where the mutated protein is derived from the HIV virus, a control sequence for HIV is HXB2. This viral genome comprises 9718 bp and has an accession number in Genbank at NCBI M38432 or K03455 (gi number: 327742).

Identifying a mutation pattern in a genetic sequence under test thus relates to the identification of mutations in the genetic sequence as compared to a wild type sequence, which lead to a change in nucleic acids or amino acids or which lead to altered expression of the genetic sequence or altered expression of the protein encoded by the genetic sequence or altered expression of the protein under control of said genetic sequence.

As noted above, the mutated protein may include only a single mutated residue.

Alternatively, the mutated protein may include a set of mutated residues comprising at least two, at least three, at least four, at least five, at least six, at least seven, at least eight, at least nine or at least ten or more mutations. A mutation pattern is a list or combination of mutations or a list of combinations of mutations. A mutation pattern of any particular genetic sequence may be constructed, for example, by comparing the tested genetic sequence against a wild type or control sequence. The existence of a mutation or the existence of one of a group of mutations can then be noted.

One way in which this may be done is by aligning the genetic sequence under test to a wild type sequence noting any differences in the alignment. Typical alignment methods include Smith-Waterman (Smith and Waterman, (1981) J Mol Biol, 147: 195-197), Blast (Altschul et al. (1990) J Mol Biol., 215 (3): 403-10), FASTA (Pearson & Lipman, (1988) Proc Natl Acad Sci USA; 85 (8): 2444-8) and, more recently, PSI-BLAST (Altschul et al. (1997) Nucleic Acids Res., 25 (17): 3389-402). It may in some circumstances be preferable to generate alignments using a multiple alignment program, such as ClustalW (Thompson et al., 1994, NAR, 22 (22), 4673-4680). Other suitable methods will be clear to those of skill in the art (see also "Bioinformatics: A practical guide to the analysis of genes and proteins" Eds. Baxevanis and Ouellette, 1998, John Wiley and Sons, New York). A practical example of multiple sequence alignment is the construction of a phylogenetic tree. A phylogenetic tree visualizes the relationship between different sequences and can be used to predict future events and retrospectively to devise a common origin. This type of analysis can be used to unravel the origin of different patient sample (i.e. the origin of the viral strain).

For example, where the mutated protein is the HIV-protease, a typical mutation pattern is 2:1, 12:V, 14:I/V, 36:D, 40:K/R, 56:K, 62:P, 76:I, with pattern:residue index-1:amino acid letter code. Where a single mutation occurs in this pattern, the residue code of the wild type or reference protein is replaced by the mutant residue code.

Where the mutation pattern is unambiguous, for example 14:I/V, one of the occurring amino-acids is preferably randomly selected to replace the wild-type or reference residue. While it is possible to use all possible combinatorial combinations of all ambiguous patterns, this is computationally more intensive and will probably not improve the prediction results.

The 3D model for the complex including the reference protein is thus adapted to allow for the mutated residue or residues of the protein which are identified as described above. Advantageously, further energy minimisation steps are then carried out to accommodate the mutated residues.

Advantageously, the 3D model may be generated from a dataset of matching genotypes and phenotypes with possible multiple phenotype measurements per genotype. In the field of drug design, there are existing databases which illustrate the matching genotype/drug resistance phenotype for various drugs. Any of such known databases may be used in the method of the present invention provided that they contain sufficient entries for each genotype/phenotype measurement for the data to be significant.

Alternatively, this 3D model may be generated from a pharmacogenomic dataset. (Maggio E. T. et al., Drug Discov. Today, 2002, 7, 1214-1220).

Where the method is to be used to predict the drug resistance phenotype conferred by a particular mutated protein, preferably the phenotypes are presented as the ratio of the drug resistance as measured by the log fold change (pFC) of the genotype in question as compared to the log fold change for the wild type reference protein. The log fold change for a particular genotype can be calculated using the formula below:

$$pFC = -\log_{10}(FC) = -\log_{10}\left[\frac{(EC_{50})_{mutant}}{(EC_{50})_{WT}}\right]$$

Wherein FC is the fold change, $(EC_{50})_{mutant}$ is the concentration of drug required to reduce the mutated protein's growth in cell culture by 50% and $(EC_{50})_{WT}$ is the concentration of drug required to reduce the wild type protein's growth in cell culture by 50%. These figures can be determined be readily determined by experimentation or by reference to readily available published data.

For example, if the protein under consideration is HIV protease, the phenotypic database may contain the phenotypic drug resistances of tested HIV viruses with a fold resistance determination compared to the reference HIV virus (wild type).

In an exemplary method of the present invention, in step (a) the three dimensional coordinates are loaded into a homology modelling program, for example, Modeler8 from Accelrys. The skilled person will, however, appreciate that any appropriate homology modelling programme may be used. By further taking into account the partner molecule and any bound solvent molecules, if present, it is possible to generate a 3D model of the complex.

The 3D models generated in step (a) are generally stored in a database prior to carrying out step (b).

The next step in the method of the present invention is to calculate the contribution of the mutated residue or set of mutated residues to the phenotype conferred by the protein. Where previously this has been done by considering only the interaction between the partner molecule and the mutated residues in question, in the method of the present invention, a number of different interactions are considered whereby a holistic analysis of the binding interaction is carried out. By adopting this methodology, it has been possible to provide surprisingly accurate predictions and, when used to predict drug resistances, it has additionally led to the identification of mutations which were previously thought to have no effect on the resistance phenotype exhibited by a particular protein to a particular drug.

A protein has a number of structural sublevels, all of which are considered in quantifying the interaction energies in the present invention. The highest level in the hierarchy is the full quaternary protein structure. Other levels commonly discussed include tertiary and secondary structural elements. Where the protein is a dimer, the structure is made up of monomeric units. Each monomeric unit of the protein is formed of chains of residues and the lowest structural unit of the protein is the residue itself.

In step (b) of the method of the present invention, the interaction energy between at least two of either (i) the protein and the partner molecule, (ii) the individual protein chains and the partner molecule, (iii) the individual protein residues and the partner molecule, (iv) the protein and the mutated residue(s) and (v) the individual protein chains and the mutated residue are considered. In previous techniques, only interaction energy (iii) has been quantified.

As noted above, by considering at least two of the above interaction energies, it is possible to make predictions which would previously have been missed using conventional techniques.

Where the protein in question normally includes bound solvent molecule(s), the interaction energy between these bound solvent molecules and the mutated residue may also be considered. More particularly, the interaction energy between the protein and partner molecule at the level of either or all of (vi) bound solvent molecule-protein, (vii) bound solvent molecule—chain, and (viii) bound solvent molecule—residue may additionally be quantified. For example, in the case of HIV protease, it is known that a water molecule is conserved near residue 50 of both chains. This water molecule may be taken into consideration when calculating the interaction energies in step (b).

Solvation of the mutated protein can be modelled in step (a) by use of a radially dependent dielectric constant. Additional methods for modelling salvation include Generalised Born (GB) or Poisson-Boltzmann (PB) techniques and may equally well be used in step (b) of the present invention.

In quantifying the interaction energies, account may be taken of van der Waals, electrostatic and Coulomb contributions. Additionally, the interaction energies may be split into the back bone and side chain contributions per residue as this may help further to identify the mechanism of action of a particular mutation.

The interaction energies are preferably quantified using an atom based or residue based force field technique. A force field is a simplified energy function, where the ability to recover good molecule energies depends on the number of parameters defined e.g. atom types, torsion angles, bond distances etc. Two well-known techniques which may be employed use parameter sets on an atom level or on a residue level. Where an atom level is used, the number of free parameters to be optimised is much larger than the number to be optimised in a residue space. A popular definition of atom parameters can be found in the Halgren, T. A. Merck, Molecular force field, J. Comp. Chem, 1998, 17, 490-641. A residue based definition can, for example, was defined by Scheraga et al., 1999; 96; 5482-5485 PNAS.

An example of a program which may be used to calculate the interaction energies is CHARMM version 3 lb available from CHARMM commercial version from Accelrys). Further examples include ICM (Molsoft) or MacroModel (Schrodinger).

Advantageously, in step (b), the accessible surface areas for the protein, chain, residue and partner molecule may be calculated. This may be done, for example, by use of any suitable method, including any of the computer programs identified above.

In addition to calculating the interaction energies in step (b), this step may include calculating further 3D model dependent and/or independent residue-specific descriptors for the residues in the mutated protein.

The term "3D model dependent residue-specific descriptor" is intended to refer to values which depend on the details of the 3D model structure, for example, the solvent accessible area of a given residue.

The term "3D model independent residue-specific descriptor" is intended to refer to all values which may be calculated without reference to 3D coordinates, for example, AAIndices.

This calculation may comprise generating a physicochemical based representation of the mutated protein using a collection of amino acid similarity matrices and amino acid indices taken from the "UMBC AAindex database"

There are a total of 494 AAindices and all of these can be used. An advantage of considering AAindices is that it may help to unravel the relevance of hydrophobic and size/volume parameters for residues which might not be unravelled by using interaction energies alone. Advantageously, in order to minimise processing time, a selection of these indices are used. Preferably the following indicies are used:

CHAM830105—The number of atoms in the side chain labelled 3+1
FAUJ880109—Number of hydrogen bond donors
PONP930101—Hydrophobicity scales
RADA880106—Accessible surface area
TSAJ990101—Volumes not including the crystallographic waters using the ProtOr
TSAJ990102—Volumes including the crystallographic waters using the ProtOr
RIER950101—Hydrophobicity scoring matrix
CSEM940101—cbsm94, Residue replace ability matrix
DOSZ010103—An amino acid similarity matrix based on the THREADER force field This is an exemplary arbitrary selection of AAIndices which covers a large number of descriptors. As the skilled person will appreciate, there are a huge number of possible combinations which may be employed successfully in this step, where included. Advantageously, a large set which covers many descriptors is selected.

The contributions calculated in step (b) are preferably stored in a database.

In step (c) of the method of the present invention, all or a subset of the contributions calculated in step (b) are compared with the equivalent contribution(s) in the at least one first reference protein complex. Advantageously, this step involves subjecting the contributions calculated to a cascade of dimensionality reduction steps in order to establish the most meaningful contributions for predicting the particular phenotype of interest conferred by the mutated protein. Generally, the cascade of dimensionality reduction steps may include steps of data set cleaning e.g. outlier reduction, missing value replacing strategy and/or normalisation, ranking or removing single features based on their information content/variance, ranking or removing features based on their correlation/divergency to other features, ranking or removing features based on their ability to predict/correlate with a problem specific value, applying the afore-mentioned steps using weighted feature sets rather than single features or, if the weighting step is not included, solving a multi-objective optimisation problem. The term "problem specific value" is used herein to refer to a value related to the phenotype under consideration. Dimensionality reduction steps are well known in the present field and any combination of appropriate techniques may be applied.

Where the phenotype under consideration is the drug resistance phenotype, advantageously, in step (c), the information content of a single feature can be measured by calculating the Shannon entropy $H_{SE}$ over the binned feature in B bins, where p is the probability that a value occurs in bin k.

$$H_{SE}(\text{feature}) = -\sum_{k=1}^{B} p(\text{bin}(\text{feature}, B, k))\log_2 p(\text{bin}(\text{feature}, B, k))$$

The full binned probability distribution for a feature over all k bins is called $P=(p_1, p_2, \ldots p_B)$. A kind of correlation coefficient can be calculated by comparing the probability distributions over two features. Here it is advantageous to use the Jensen-Shannon divergency $D_{JS}$ $$D_{JS}(P, P') = H_{SE}\left(\frac{1}{2}(P - P')\right) - \frac{1}{2}[H_{SE}(P) - H_{SE}(P')]$$

Features with a low information content $H_{SE}$ can be removed. Depending on the phenotype under consideration, very diverse feature with high $D_{JS}(P, P')$ or very similar features with a low $D_{JS}(P, P')$ value can be selected.

Where the phenotype conferred is measured by reference to the pFC value of the mutated protein, feature selection algorithms may also be used to select problem specific features:

$$I_G(P, pFC) = H_{SE}(P) - H_{SE}(P|pFC)$$

While each of these steps are known in isolation in the field of bioinformatics, they have not been used in combination previously in combination with molecular modelling techniques. The individual steps are ones with which the skilled person is familiar. In this regard, for further detail, reference is made to Cover T. M. & Thomas, J. A., Elements of Information Theory, John Wiley and Sons. Inc., 1991 or Kapur J. N. Measures of information and their applications, John Wiley and Sons, Inc., 1994.

Where a cascade of dimensionality reduction steps have been applied, the result is a reduced set of contributions, all of which are considered to be meaningful to the prediction of the phenotype conferred by the mutated protein. Thus the computational power and memory requirements are reduced because a smaller dataset is to be considered. This reduced data set can then advantageously be used to create a single prediction in step (d). To generate a prediction, advantageously, one or more algorithms are applied to the data. Advantageously at least one linear regression technique is used in this step. In general terms, linear regression is a technique for modelling the conditional expected value of one variable given the value of some other variable or variables. Using this technique, it is possible to build regression models.

A further algorithm which may be applied is a decision tree. A decision tree is a rule based learning scheme which uses principles from information theory to select a highly predictable root node followed by branching nodes. These techniques are also known as "recursive partitioning" in the fields of modelling and cheminformatics.

Furthermore, weighted and unweighted mixtures of single models known as voting meta-learner algorithms may be applied. An example of a suitable weighted meta-learning algorithm is the AdaBoost.M1 which allows for a reweighting of data instances where values have not been predicted well.

These steps deliver single feature rankings or multiple feature set rankings which can be used to assign a quantitative phenotype.

Advantageously, two interpretations may be used, specifically single feature rankings before applying the learning method (such as, for example, linear regression or decision trees) and a statistical ranking over multiple feature sets. It is clear for feature sets that the relevance of a single feature can be only calculated in the context of the other features in this set. Since there exists for N features in theory $2^N$ possibilities to create sets it is clear that for larger sets only a statistical sampling over all possible sets can be evaluated. Preferably, the best feature sets returned by the best model or the best ensemble of models are used. It has been observed that using an ensemble of models increases the reliability of feature rankings, since slightly diverse feature sets might be used for the ensemble models. In fact, the use of an ensemble model only has an additional value, if the underlying predictions and features are diverse. Otherwise exactly the same predictions would be obtained. This principle is known as the 'Epicur principle'.

By comparison of the predictions and feature sets for phenotype predictions, it is possible to identify single residues or sets of residues which are important in determining the phenotype conferred by the protein when interacting with one partner molecule but not when interacting with a different partner molecule. For example, where the method is applied to predict drug resistance phenotypes, it is possible to identify single residues or sets of residues which cause high resistance for a particular drug but not for another drug.

The methods of the present invention may be repeated for a given mutated protein with a number of different partner molecules and similarly with a given partner molecule and a number of different mutated proteins. In doing so, a database of phenotype predictions may be generated. Accordingly in a further aspect of the present invention, there is provided a database containing information relating to the predicted individual contribution of a mutated residue or set of mutated residues in a protein to the phenotype conferred by that protein, said database being generated by performing a method as described above. Preferably this database comprises phenotype predictions for all known protein structures pre-calculated according to the methods of this invention. In this way, the database may be accessed and, for example, a request for information relating to those protein structures which are resistant to a particular drug may be entered.

Where they are used to generate drug resistance phenotype predictions, the methods of the present invention are therefore useful in assessing the efficiency of a patient's therapy or in optimising therapy.

According to a further aspect of the present invention, there is provided a diagnostic system for optimising a drug therapy in a patient, comprising performing a method as herein described for each drug or combination of drugs being considered to obtain a series of drug resistance phenotypes and therefore assess the effect of the drug or combination of drugs on the resistance exhibited by the pathogen with which the patient is infected and selecting the drug or drug combination for which the pathogen is predicted to have the lowest resistance.

Such a method is particularly advantageous where the pathogen is an HIV strain.

According to a further aspect of the present invention, there is provided a diagnostic system for predicting the individual contribution of a mutation or a set of mutations in a protein to the drug resistance phenotype conferred by that protein, said system comprising:
(a) means for obtaining a genetic sequence of said mutated protein;
(b) means for identifying the mutation pattern in said genetic sequence as compared to a reference protein; and
(c) means for predicting the phenotype conferred by said protein using any one of the methods as described herein.

The genetic sequence of the mutated protein and the mutation pattern in said genetic sequence may be determined as described above.

The means for predicting the phenotype conferred by the protein are preferably computer means.

Advantageously, the mutated protein is an HIV strain.

A still further aspect of the present invention relates to a computer apparatus or computer-based system adapted to perform any one of the methods of the invention described above, for example, to quantify the individual contribution of a mutated residue or set of mutated residues to the phenotype exhibited by a mutated protein.

In a preferred embodiment of the invention, said computer apparatus may comprise a processor means incorporating a memory means adapted for storing data; means for inputting data relating to the mutation pattern exhibited by a particular protein; and computer software means stored in said computer memory that is adapted to perform a method according to any one of the embodiments of the invention described above and output a predicted quantified drug resistance phenotype exhibited by the protein possessing said mutation pattern.

A computer system of this aspect of the invention may comprise a central processing unit; an input device for inputting requests; an output device; a memory; and at least one bus connecting the central processing unit, the memory, the input device and the output device. The memory should store a module that is configured so that upon receiving a request to quantify the individual contribution of a mutated residue or set of mutated residues to the drug resistance phenotype exhibited by the protein, it performs the steps listed in any one of the methods of the invention described above.

In the apparatus and systems of these embodiments of the invention, data may be input by downloading the sequence data from a local site such as a memory or disk drive, or alternatively from a remote site accessed over a network such as the internet. The sequences may be input by keyboard, if required.

The generated results may be output in any convenient format, for example, to a printer, a word processing program, a graphics viewing program or to a screen display device. Other convenient formats will be apparent to the skilled reader.

The means adapted to quantify the individual contribution of a mutated residue or set of mutated residues to the drug resistance phenotype exhibited by the protein will preferably comprise computer software means. As the skilled reader will appreciate, once the novel and inventive teaching of the invention is appreciated, any number of different computer software means may be designed to implement this teaching.

According to a still further aspect of the invention, there is provided a computer program product for use in conjunction with a computer, said computer program comprising a computer readable storage medium and a computer program mechanism embedded therein, the computer program mechanism comprising a module that is configured so that upon receiving a request to quantify the individual contribution of a mutated residue or set of mutations to the drug resistance phenotype exhibited by the protein it performs the steps listed in any one of the methods of the invention described above.

The invention further relates to systems, computer program products, business methods, server side and client side systems and methods for generating, providing, and transmitting the results of the above methods.

The invention will now be described by way of example with particular reference to a specific algorithm that implements the process of the invention. As the skilled reader will appreciate, variations from this specific illustrated embodiment are of course possible without departing from the scope of the invention.

The invention and example will be further described by reference to the figures in which.

Figure 4:
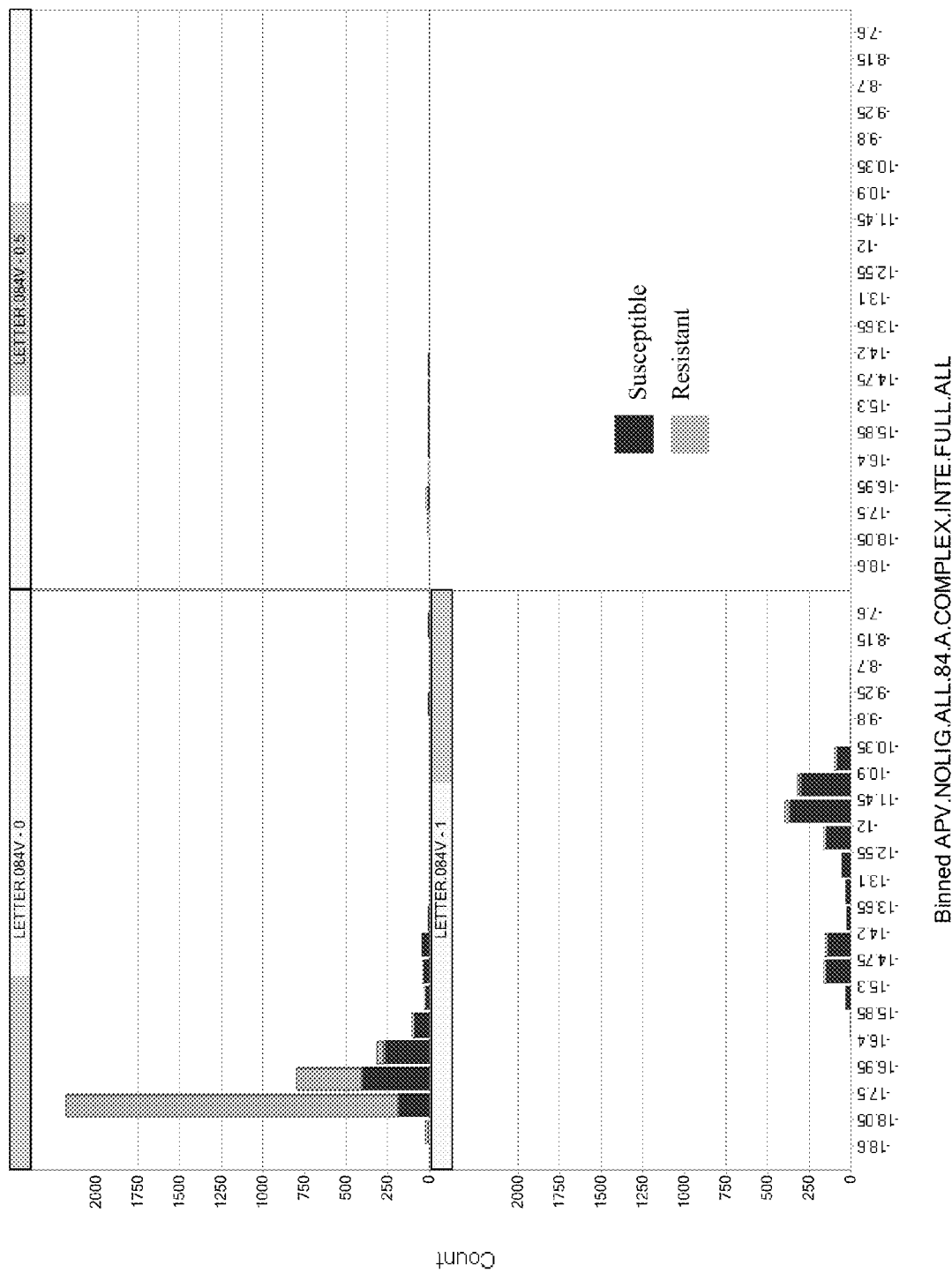
Figure 5:
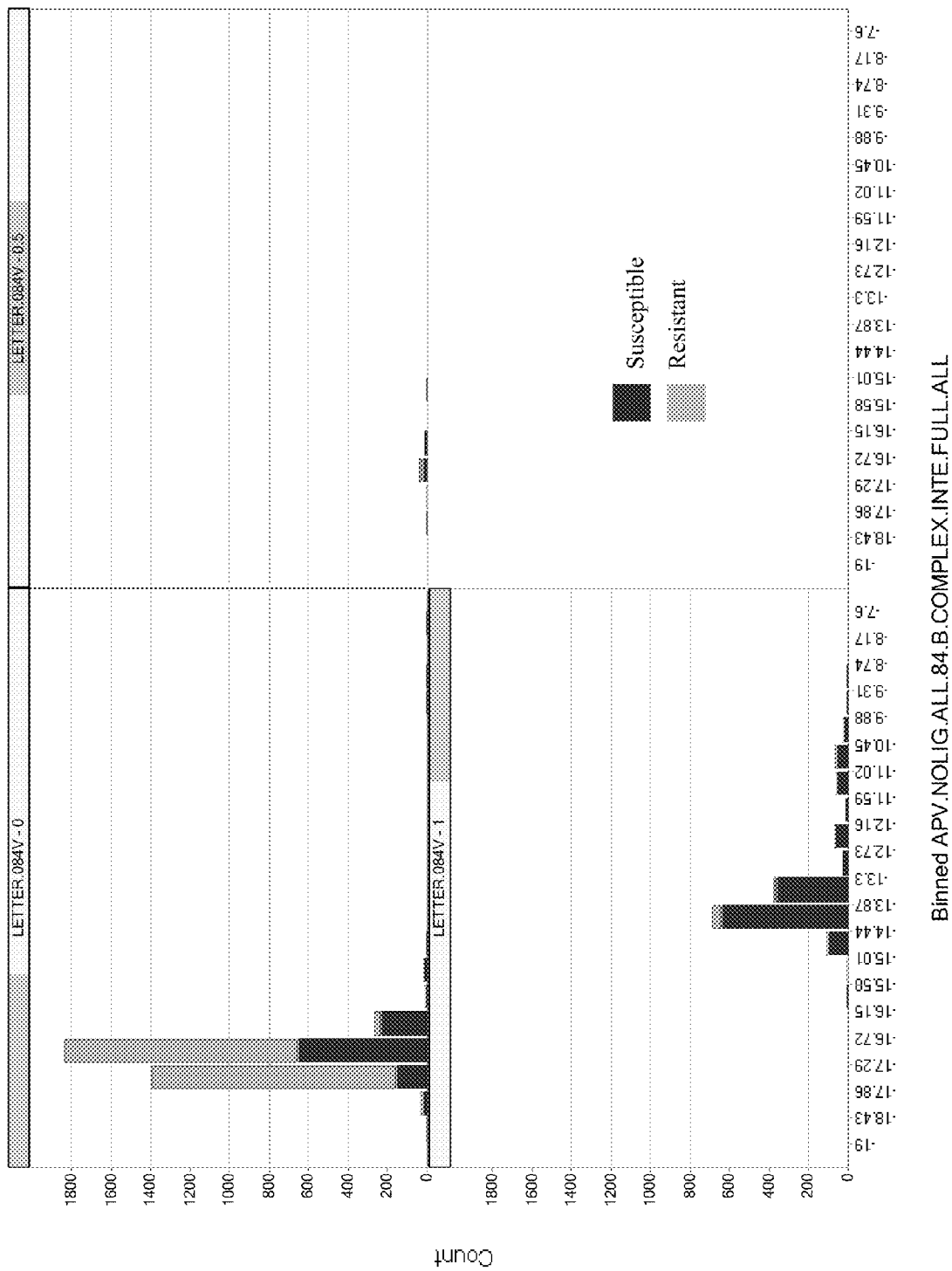
Figure 6:
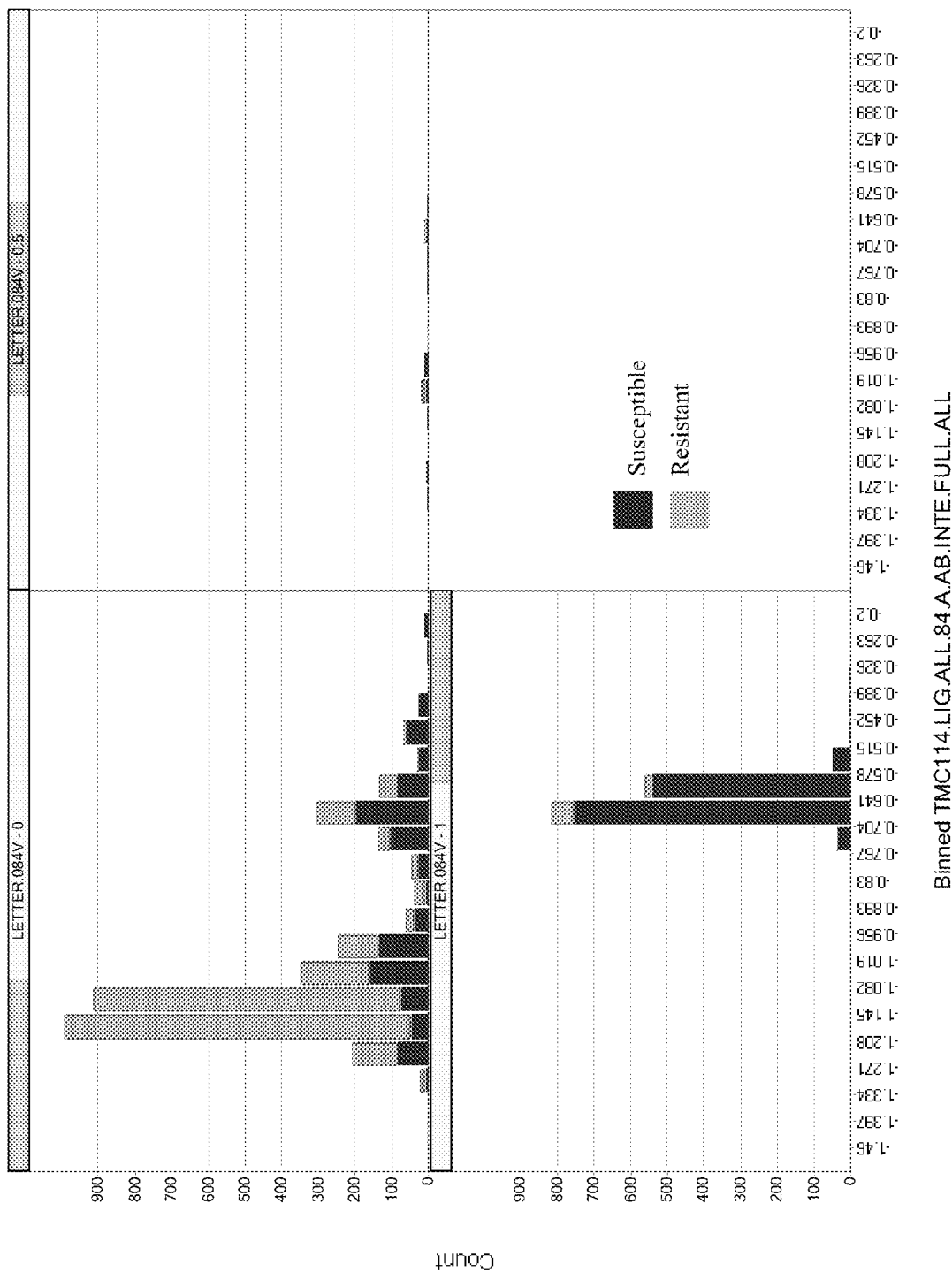
Figure 7:
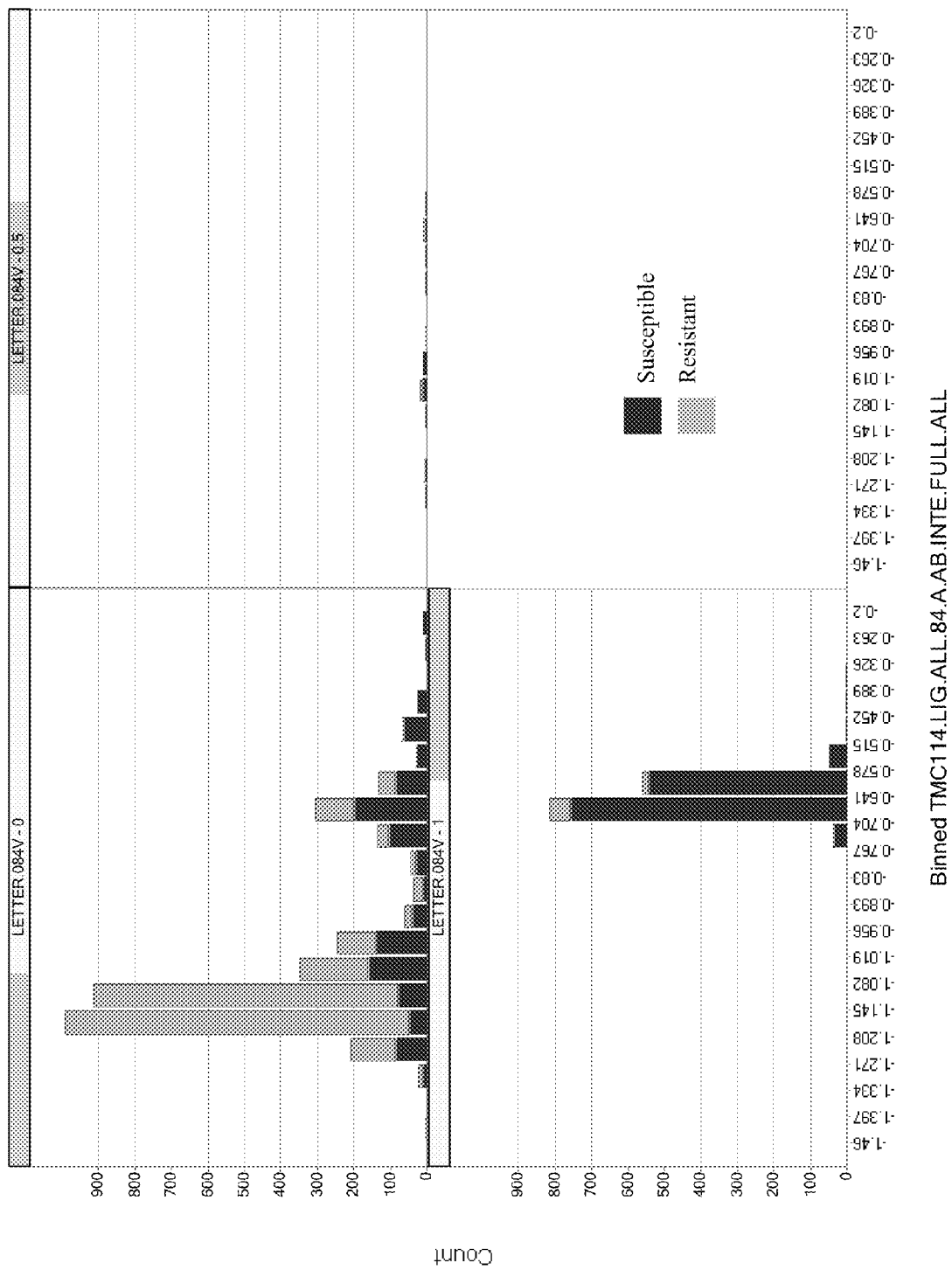
Figure 8:
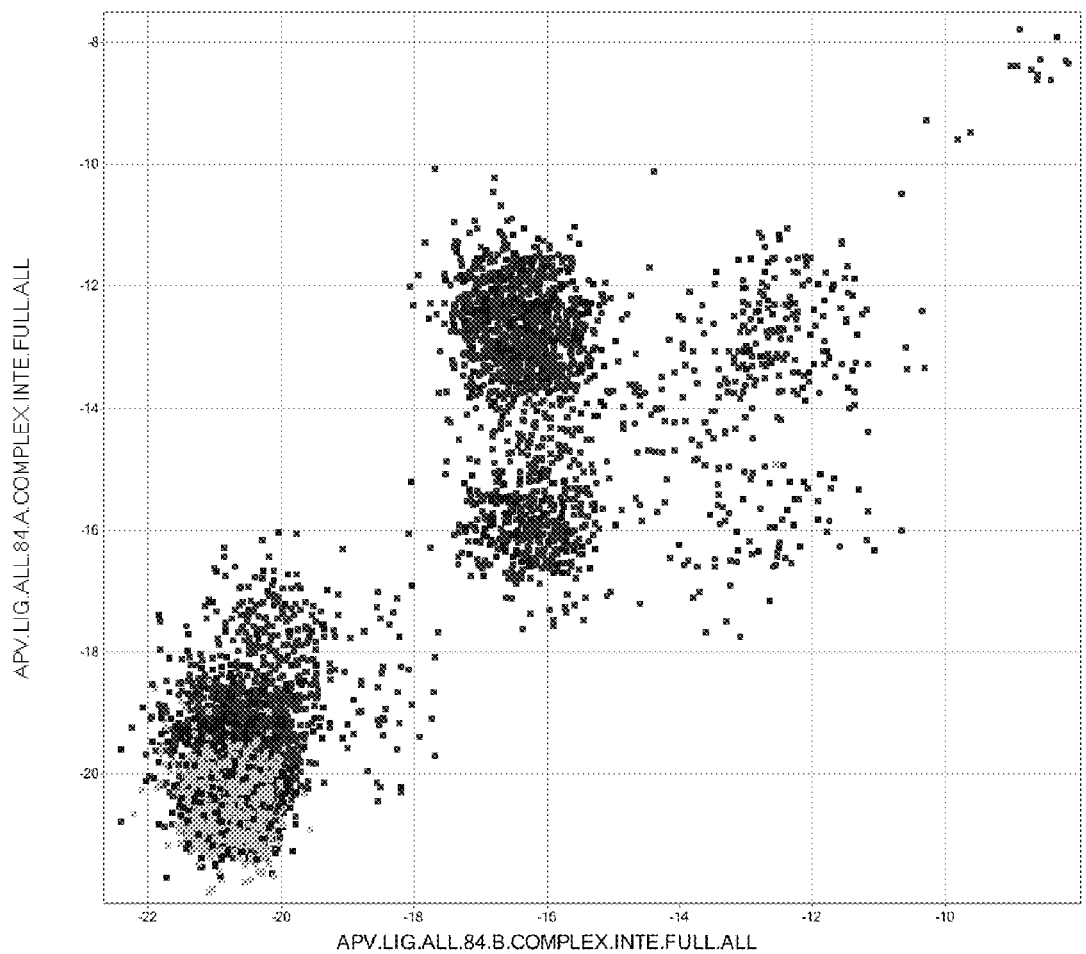
Figure 9:
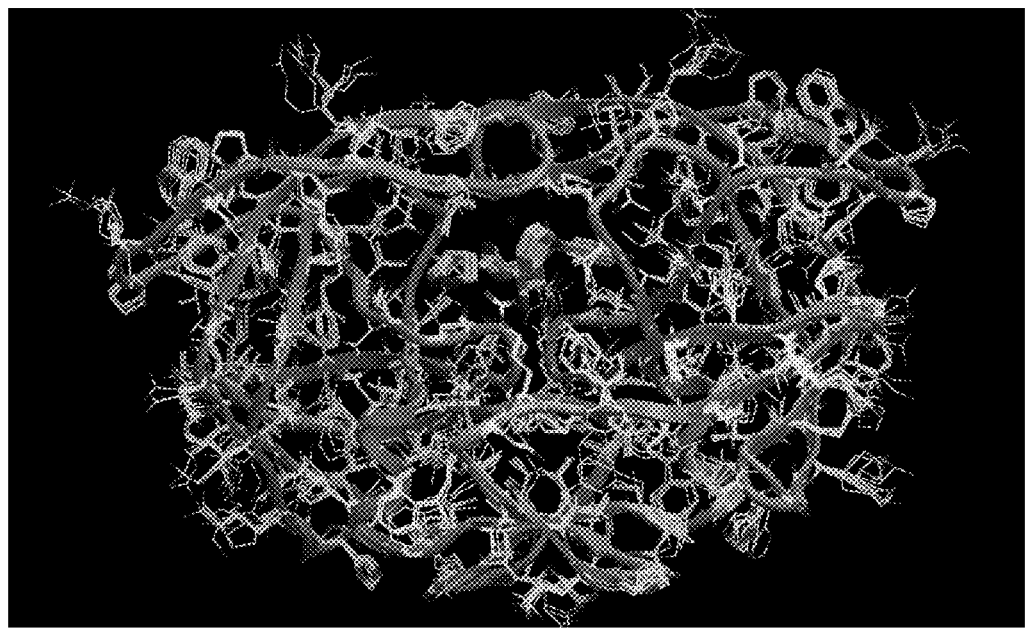
Figure 10:
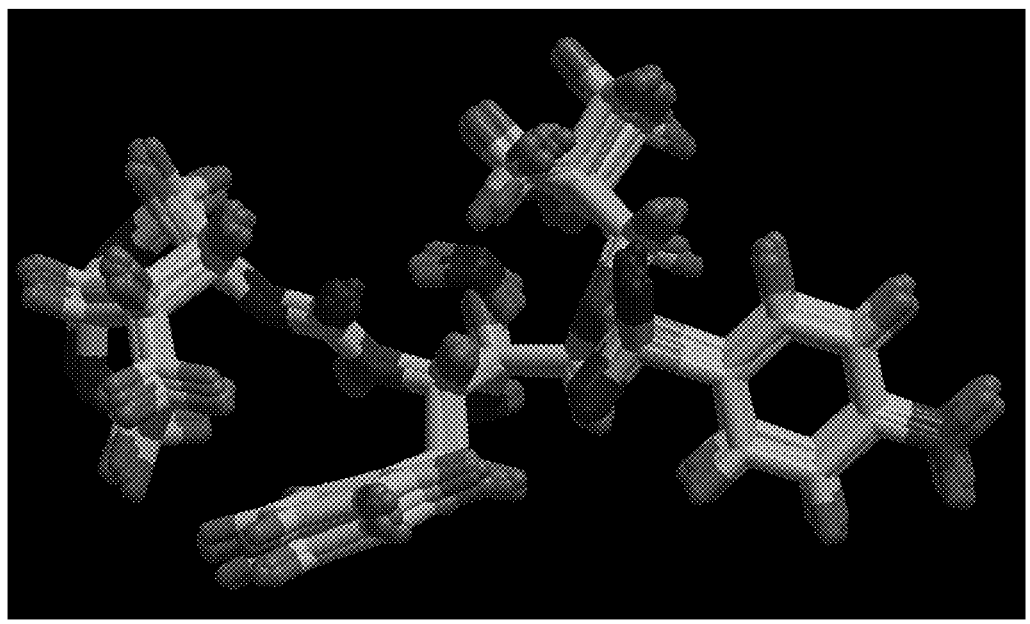
Figure 11:
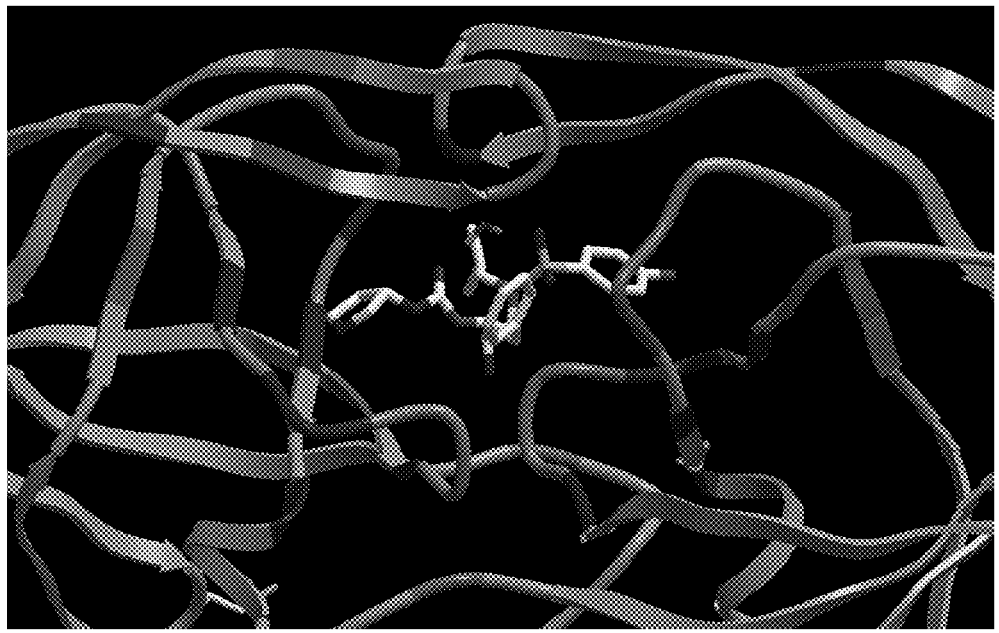
Figure 12:
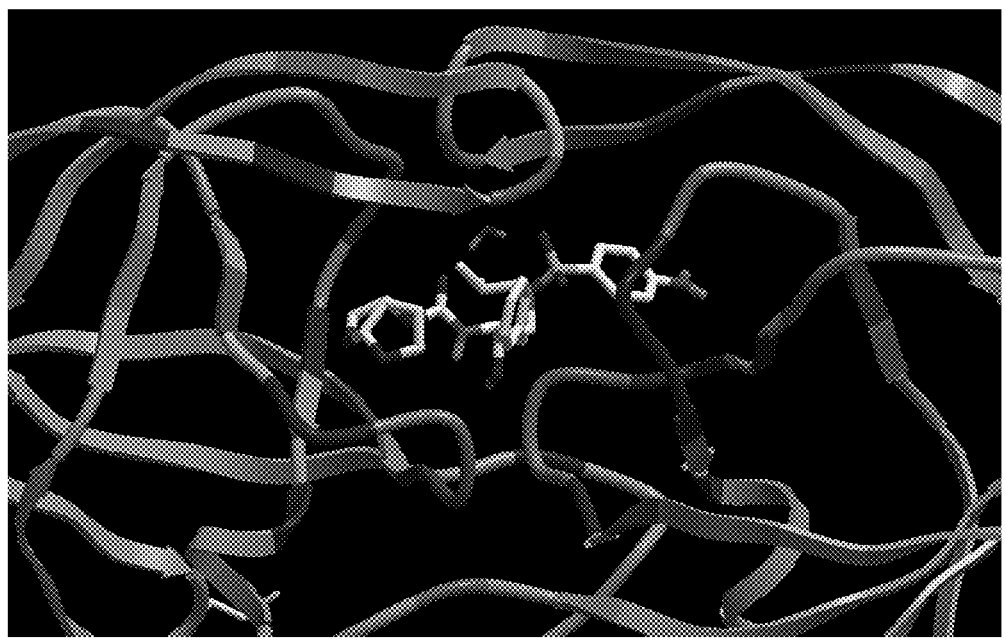

FIG. 4 illustrates the Amprenavir homology model, but the partner molecule was removed for calculating the interaction residue-complex energies for residue 84 in protein chain A. Letter.084V=0 represents a mutant structure having an Ile at position 84 and mutants represented by Letter.084V=1 have a Val at position 84;

FIG. 5 illustrates the Amprenavir homology model, but the partner molecule was removed for calculating the interaction residue-complex energies for residue 84 in protein chain. Letter.084V=0 represents a mutant structure having an Ile at position 84 and mutants represented by Letter.084V=1 have a Val at position 84;

FIG. 6 shows the Amprenavir interaction residue-complex interaction energies for residue 84 in protein chain A. Letter.084V=0 represents a mutant structure having an Ile at position 84 and mutants represented by Letter.084V=1 have a Val at position 84;

FIG. 7 shows the Amprenavir interaction residue-complex interaction energies for residue 84 in protein chain B. Letter.084V=0 represents a mutant structure having an Ile at position 84 and mutants represented by Letter.084V=1 have a Val at position 84;

FIG. 8 shows the Amprenavir interaction residue-complex interaction energies for residue 84 separated by protein chain A and B and illustrates the asymmetric protein complex behaviour of the HIV protease homodimer;

FIG. 9 illustrates the sample diversity mutant panel set based on 3D atom placement diversity;

FIG. 10 shows the view on the structural water and partner molecule Darunavir in a set of diverse 3D models based on amino acid mutant patterns;

FIG. 11 illustrates the Amprenavir protein complex using only the interaction energies of one residue with the full protein, water and partner molecule complex; and FIG. 12 illustrates the Amprenavir protein complex using only the interaction energies of one residue with the full protein, water and partner molecule complex.

EXAMPLES

Methodology

A dataset of matching genotype/phenotype measurements was used with possible multiple phenotype measurements per genotype and including a total of 11905 experimental values. Phenotypic resistance information can be either assessed directly or by phenotypic assays in which recombinant virus techniques directly measure viral replication in the presence of increasing drug concentrations (Hertogs, K.; de Bethune, M.-P.; Miller, V.; Ivens, T.; Schel, P.; van Cauwenberghe, A.; van den Eynde, C.; van Gerwen, V.; Azijn, H.; van Houtte, M. *Antimicrob. Agents Chemother.* 1998, 42, 269-276 and Walter, H.; Schmidt, B.; Korn, K.; Vandamme, A. M.; Harrer, T.; berla, K. Rapid, *J. Clin. Virol.* 1999, 13, 71-80). Alternatively they may be deduced from genotypic assays that are based on sequencing of the relevant parts of the viral genome (Vandamme, A. M., Van Laethem K., De Clerq, Drugs 1999, 57, 337 to 361).

The mutation patterns are all defined relative to HXB2 at amino acid level.

HXB2
PQVTLWQRPLVTIKIGGQLKEALLDTGADDTVLEEMSLPGRWKPKMIGGI

GGFIKVRQYDQILIEICGHKAIGTVLVGPTPVNIIGRNLLTQIGCTLNF

In the present example, the genotype/phenotype data was extracted from an in-house HIV genotype/phenotype database. The phenotypes were presented as pFC values, wherein the pFC is equal to −log(FC), where FC denotes the fold change (also fold resistance, FR). Negative pFC values denote resistance and positive values denote hyper-susceptibility. For example, a pFC value of −1 is equal to 10-fold resistance.

Figure 1:
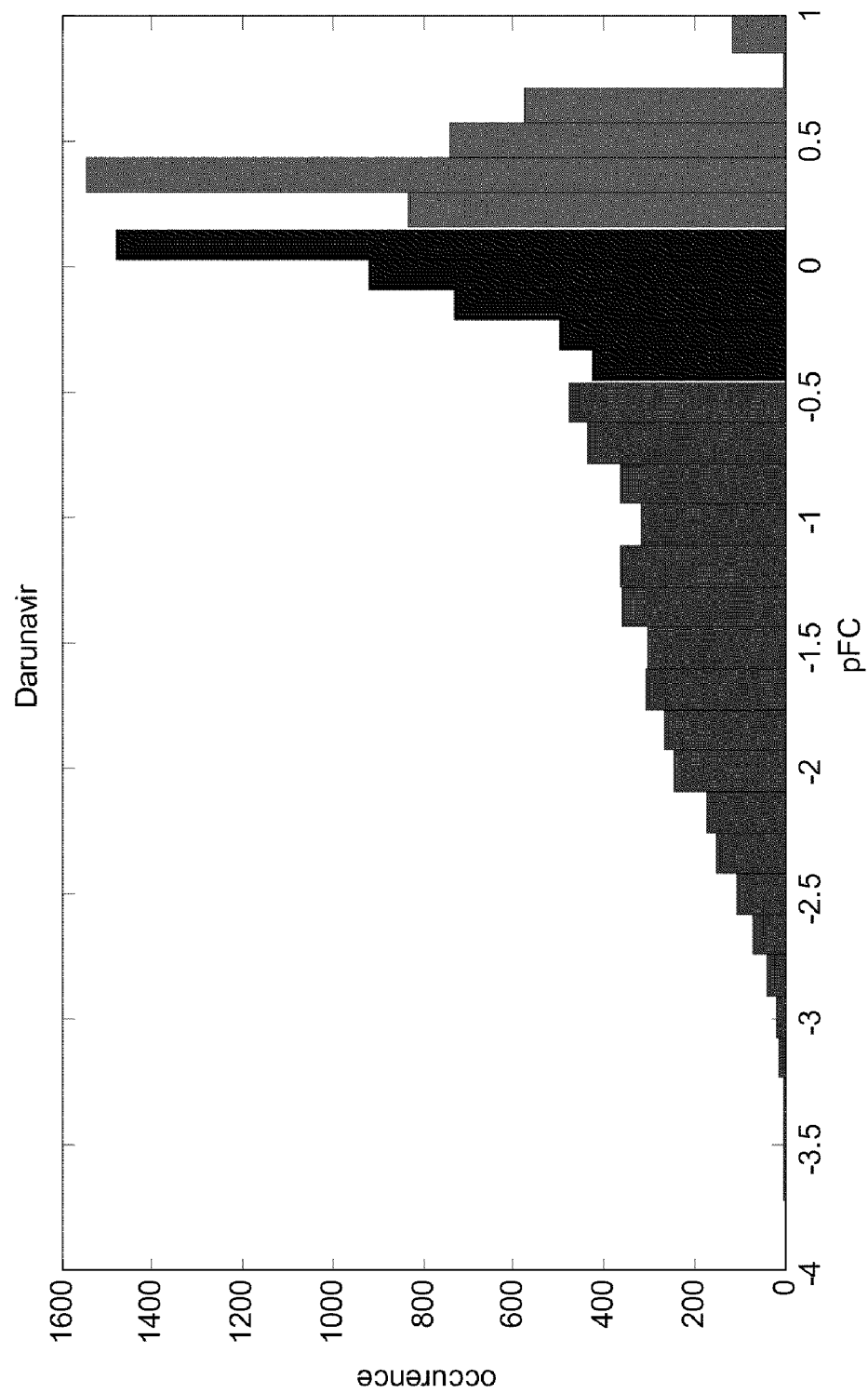
FIG. 1 shows the distribution of pFC values for Darunavir.
Figure 2:
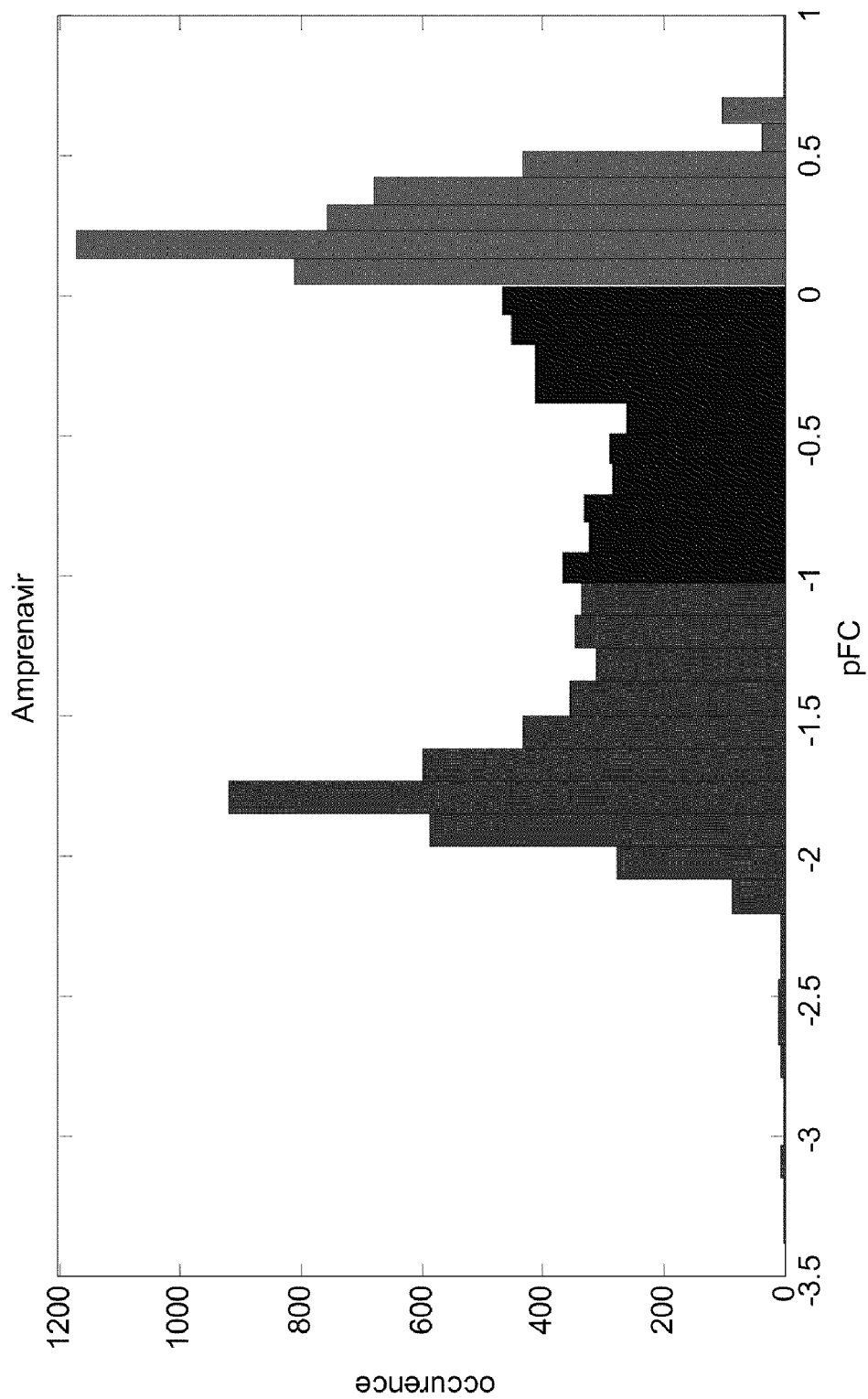
FIG. 2 shows the distribution of pFC values for Amprenavir.
Figure 3A:
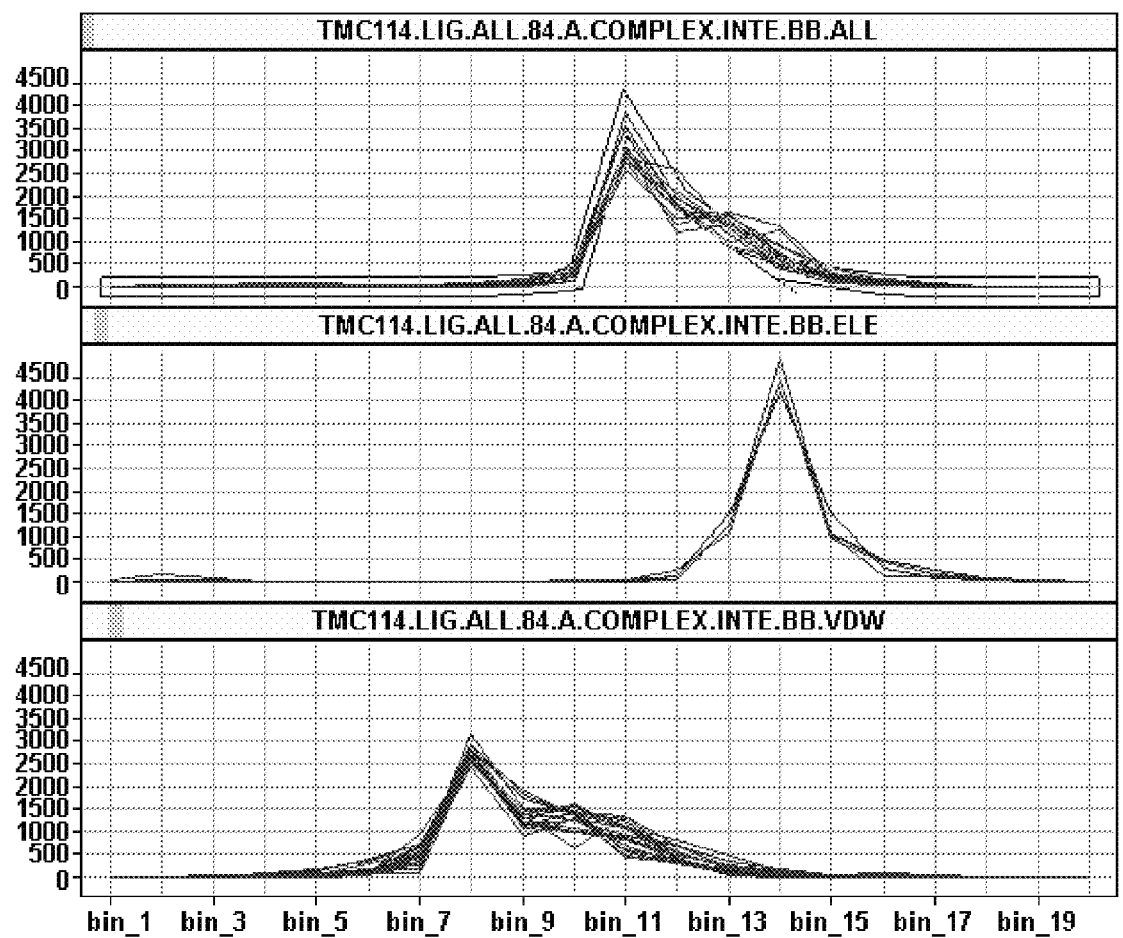
FIG. 3 shows a profile view for some interaction energy feature correlations for residue 84 of the partner molecule Darunavir.
Figure 3B:
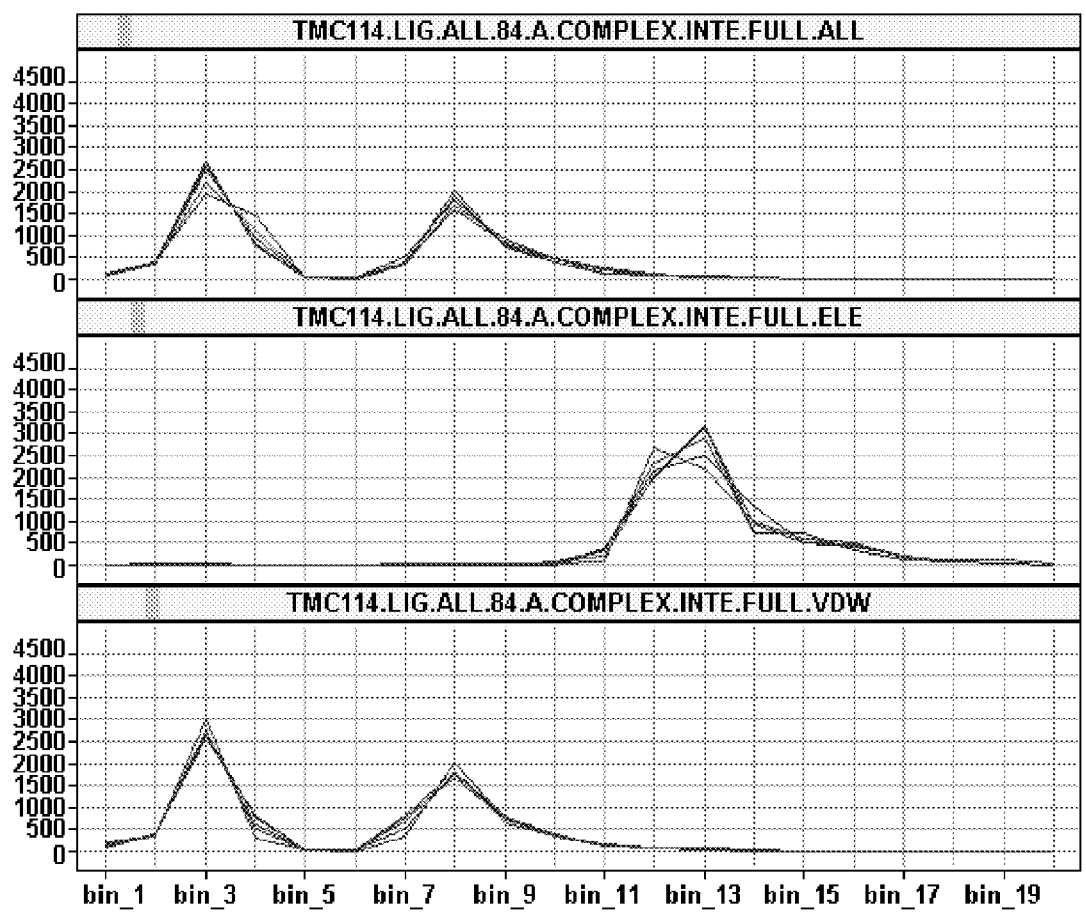
Figure 3C:
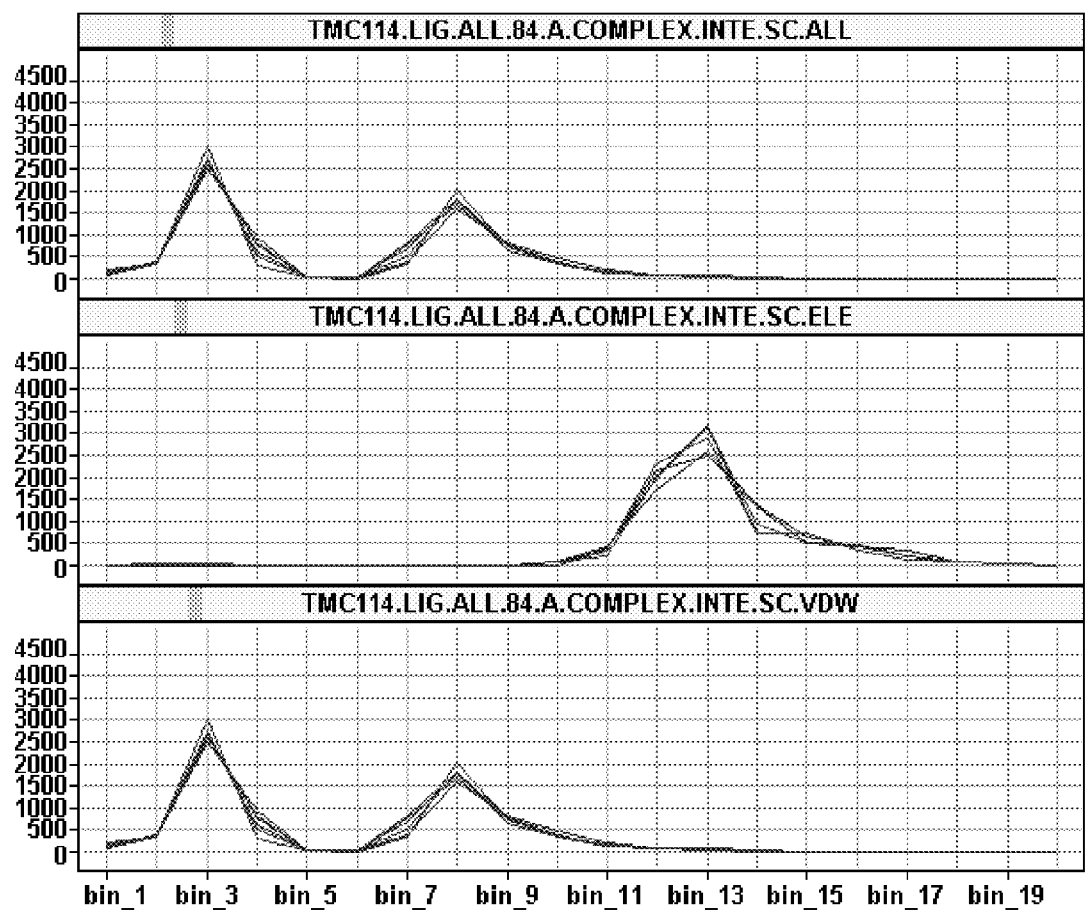
Figure 3D:
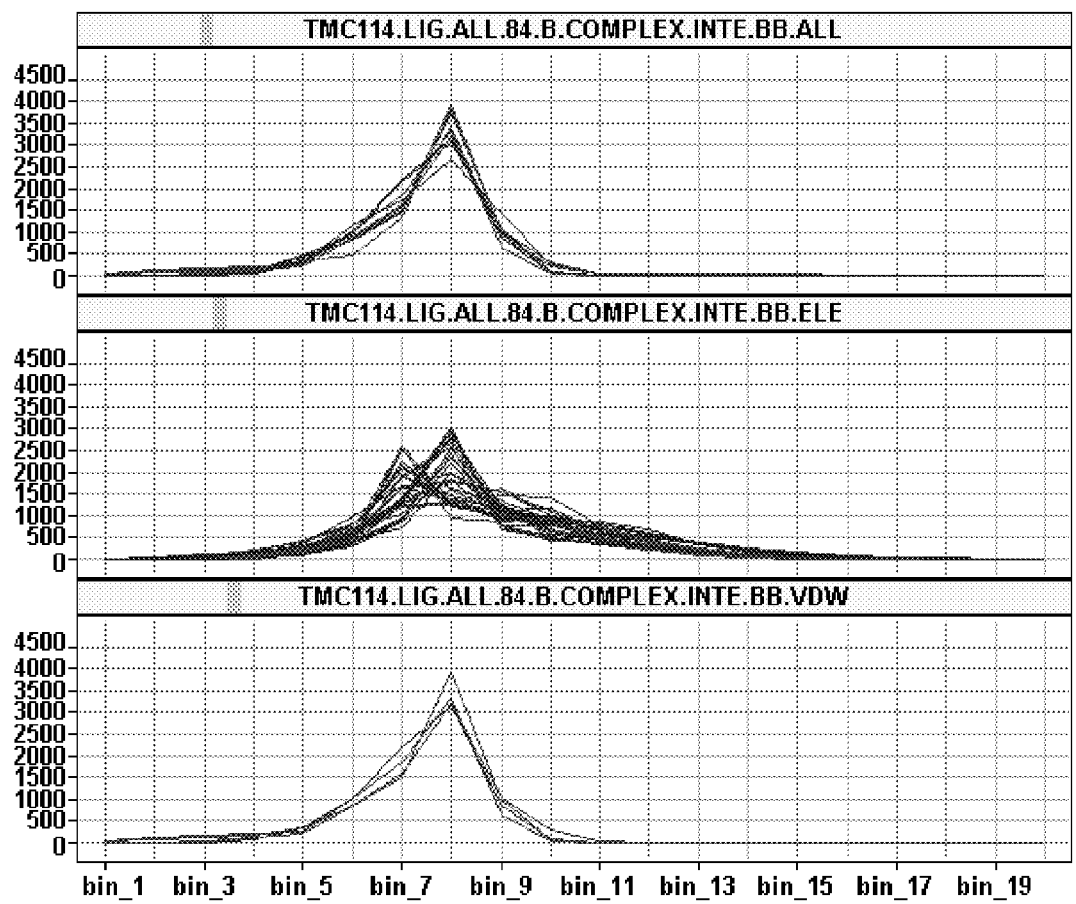
Figure 3E:
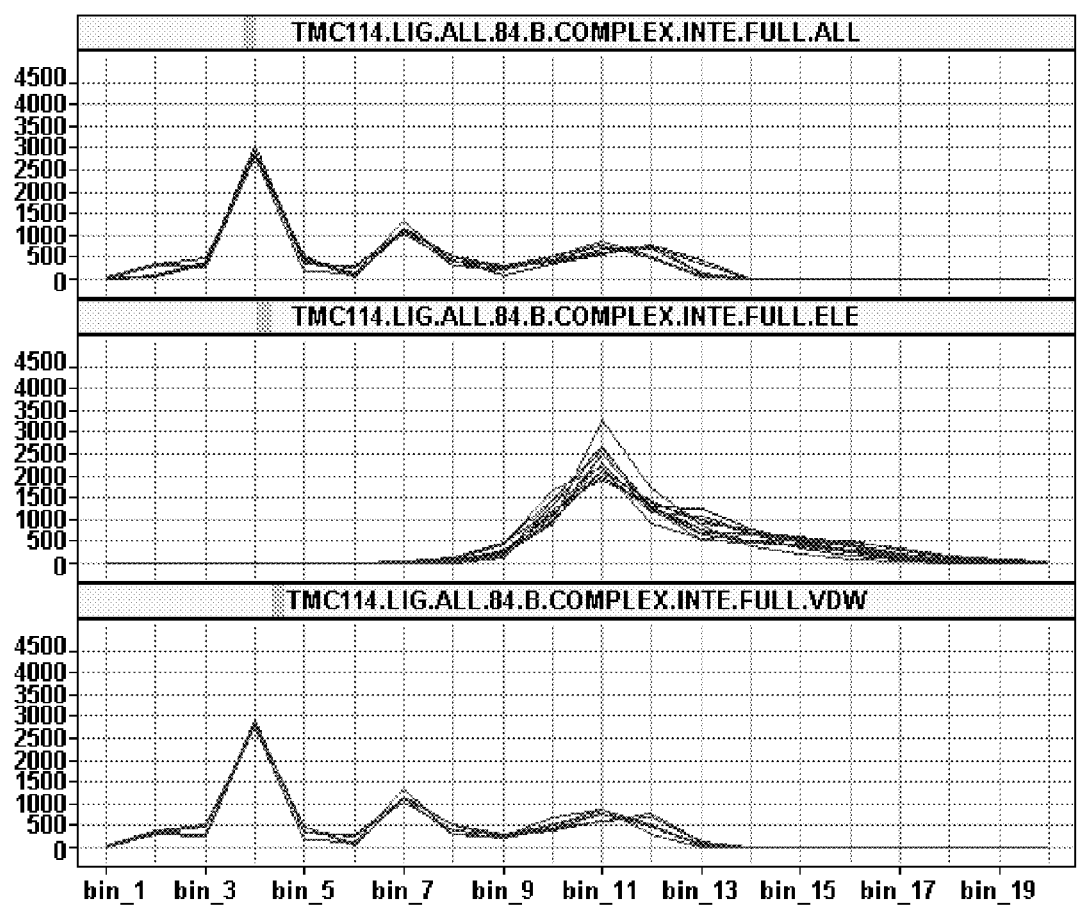
Figure 3F:
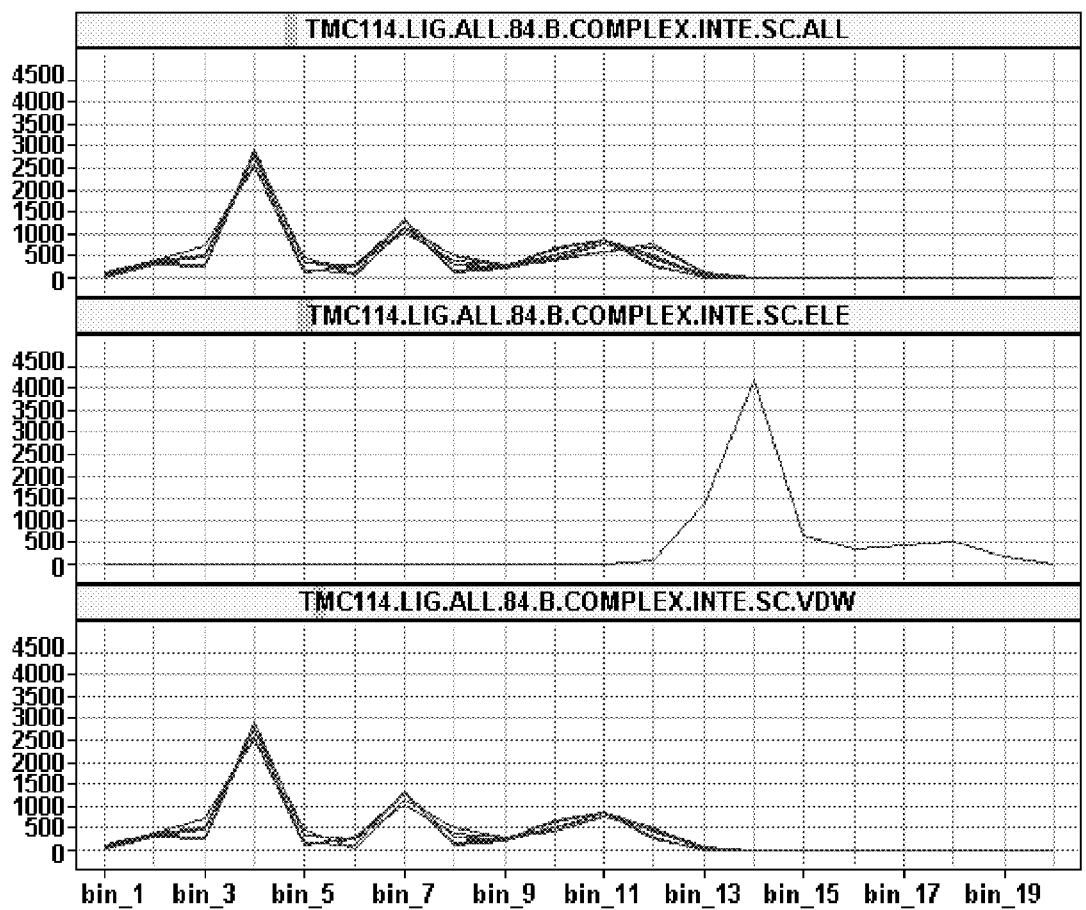
Figure 3G:
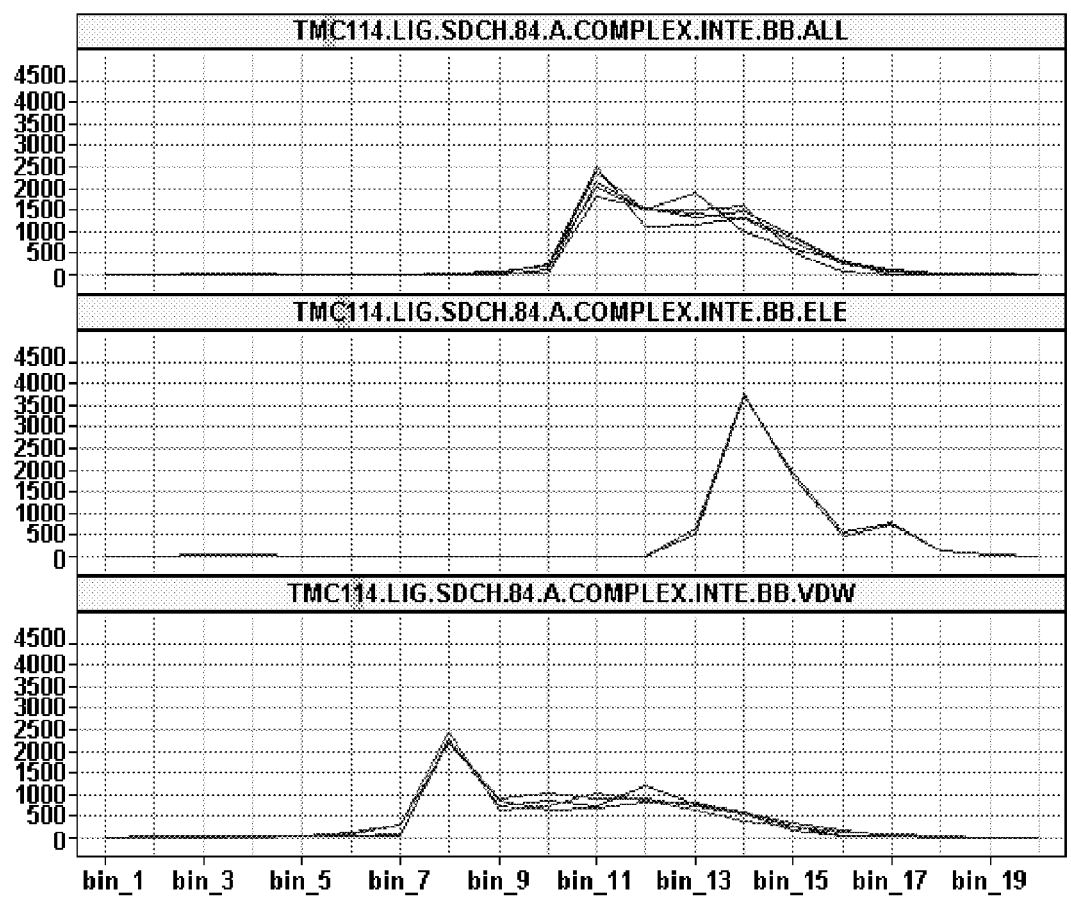
Figure 3H:
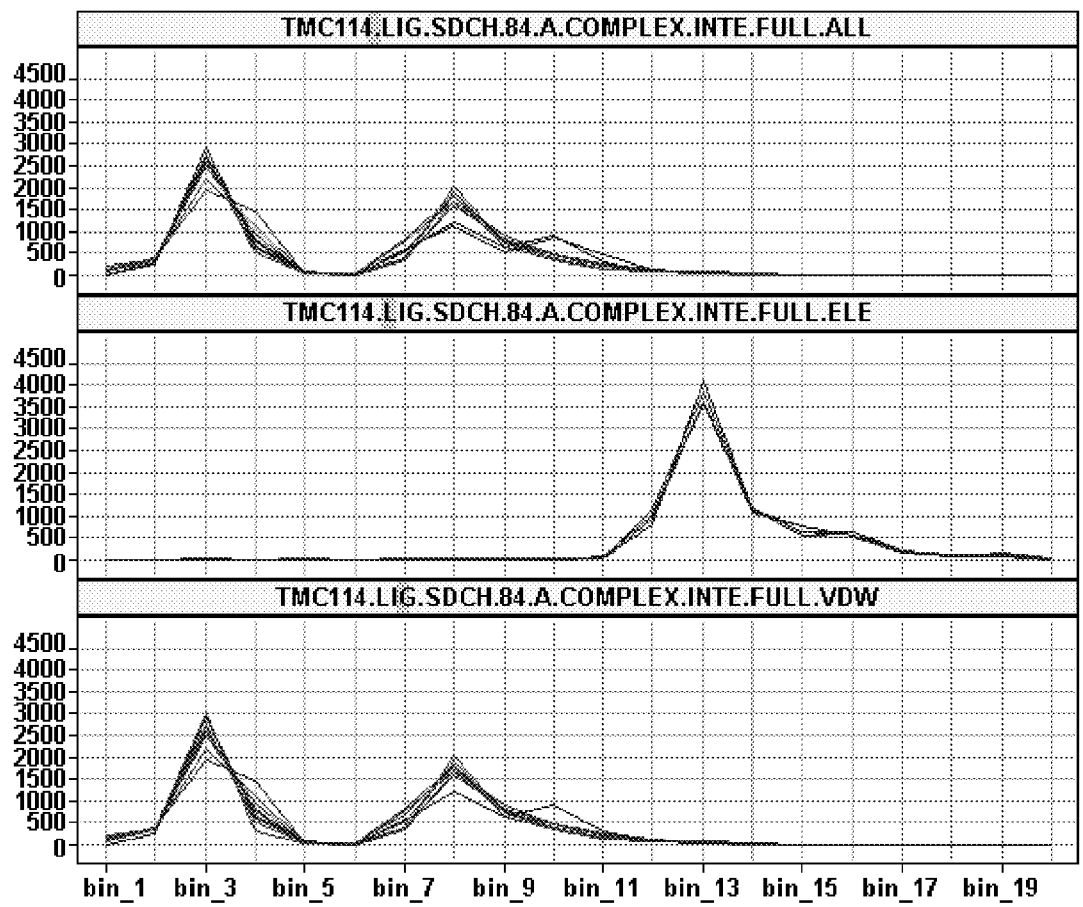
Figure 3I:
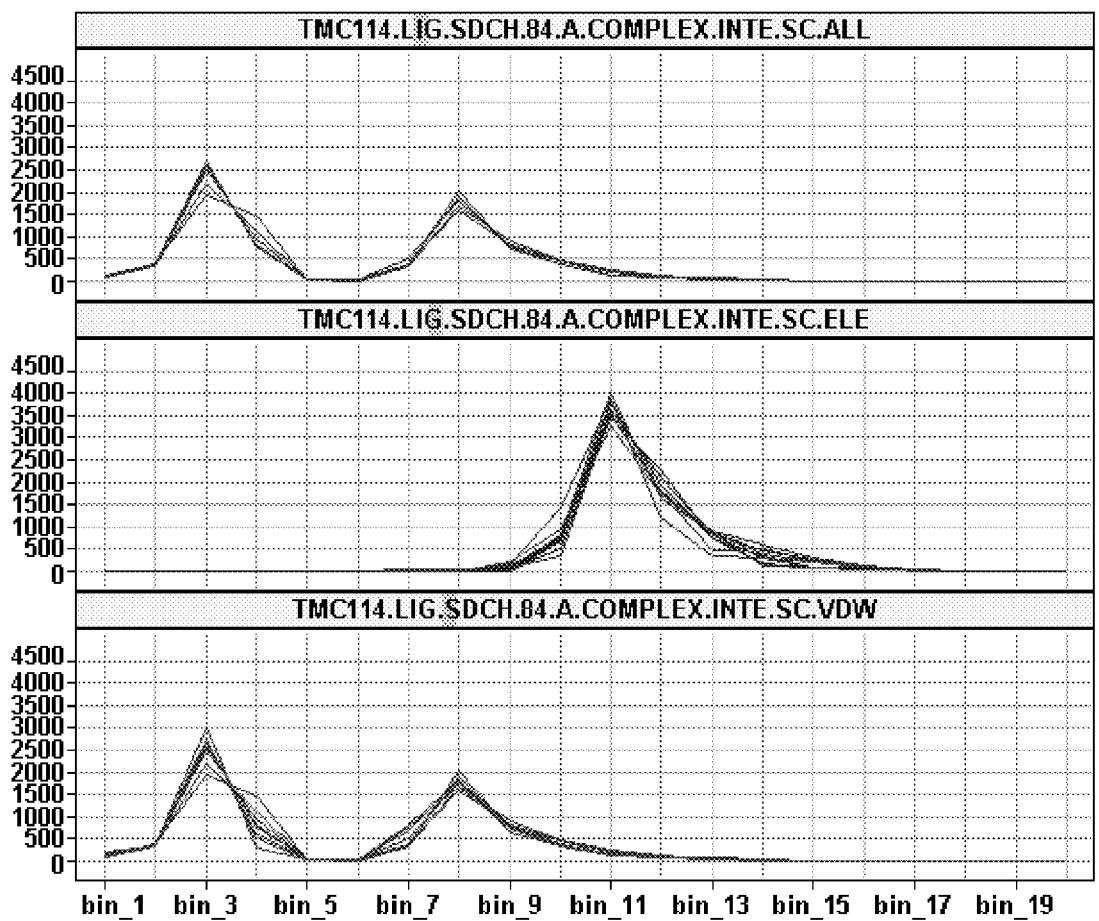
Figure 3J:
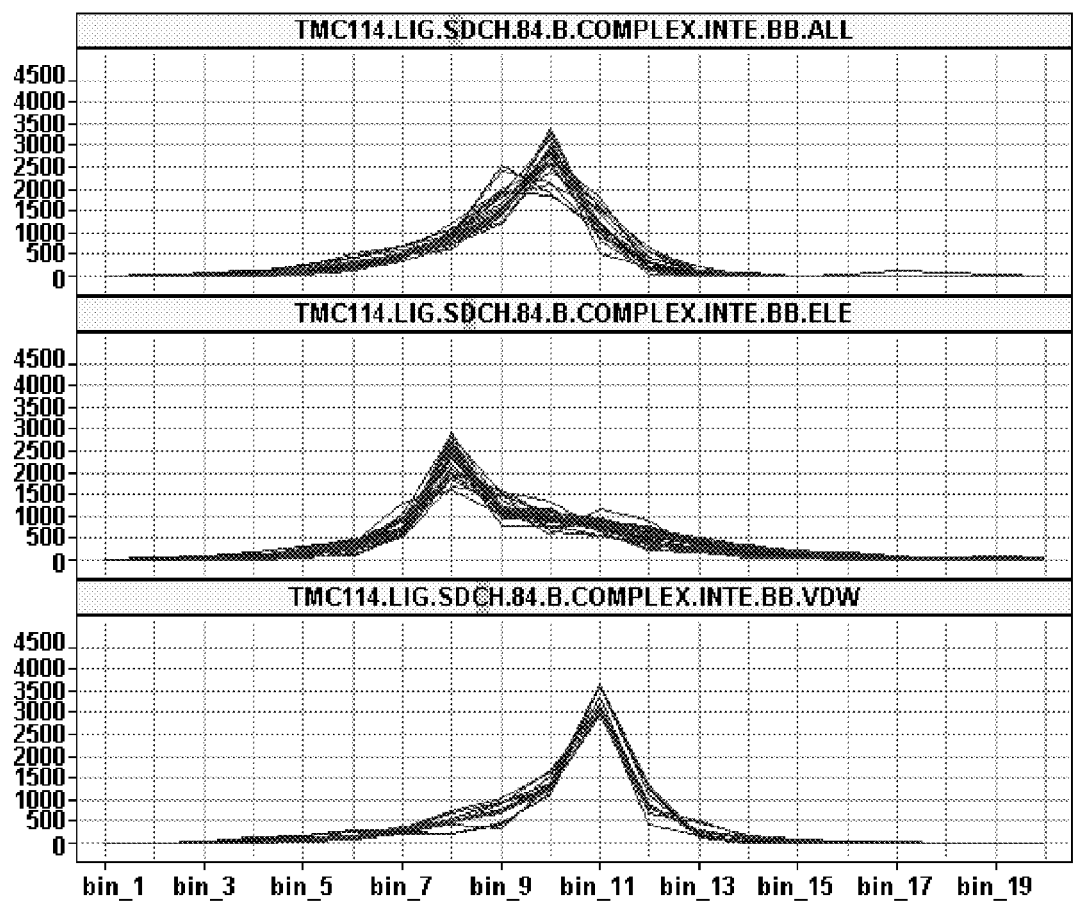

The value distributions for the pFC phenotype for the partner molecules Darunavir and Amprenavir are illustrated in FIGS. 1 and 2. The classification in two and three classes is based on an equal frequency binning avoiding skewed class distributions. On the basis of these value distributions one would suggest that it is easier to discriminate between highly resistant residues mutant strains and susceptible mutant strains for Amprenavir than for Darunavir, which can be confirmed by building prediction models.

Considering whether the binary prediction model for Darunavir is better than the Amprenavir model, the binary classification rates are calculated as 90% and 96% respectively using only the highly resistant and the susceptible strains and by taking only the 1000 complex interaction energies with the highest information content into account.

Two X-ray determined protein 3D structures of HIV protease with a partner molecule were used. In one complex the partner molecule was Amprenavir (PDB:1hpv) and in the other it was Darunavir (non-public crystal structure). Although a non-public crystal structure of Darunavir was used in this example, there are a large number of publicly available crystal structures for this partner molecule.

Reference structures were generated by modifying the structures by:
  changing residues in the 3D structure to have an identical HXB2 sequence (wild-type) by using energy minimization.
  keeping only the structural flap water interaction on both cases with the partner molecules 3D Molecular Modelling and Statistical Modelling Starting from the HXB2 amino acid sequence and the two 3D reference structures with partner molecules, 3D models $M_{3d}$ were created for all genotypes in the data set with the following parameters:

$M_{3d}$(referenceprotein, partnermolecule, mutationpattern, H)

An exemplary model generation is detailed below:

$M_{3d}$(HXB2, Ampranavir, (I3V, D63L, I84V),

H=(optimizesidechains=yes, sphericrelaxation=yes, ... ))

where H is a set of parameters relevant for the 3D model generation. These parameters describe e.g., the homology modelling protocol applied for the given mutation pattern. In this case fixed backbone and a flexible backbone have been used;
  the optimization protocol and constraints applied to the single residues of the mutation pattern when using the reference structure. In the present case, a spherical region around each mutated residue was energetically minimized;
  the energy minimization protocol used for the homology model generation;
  the solvation model used. In the present example, a distance dependent dielectric field was assumed;
  whether or not the energy refinement step should include the partner molecule or not (apo reference structure). In the present example, both cases have been calculated; and
  the type of energy minimization used for refining the basic homology model. In the present example a hybrid cascade of a steepest descent (SD) minimization followed by an adopted basis newton-raphson (ABNR) minimization was used.

After the generation of a 3D model for each mutation pattern of the genotype/phenotype data, a feature vector was calculated. This vector uses different levels of interaction energies for protein residues covering different effects, for example:

interactions between protein, water, partner molecule, and full complex;
  contribution to interaction energy, further specified as backbone, sidechain, and full residue contribution;
  surface area calculation;
  including or excluding partner molecule.

The feature vector was extended by calculating for each mutation pattern the AAIndices given in the description at page 15, relating to mainly residue hydrophobicity and residue volume.

The final feature vector contained 28987 features for one single mutation pattern. This number was obtained for each protein complex with partner molecule, thus resulting in a total of 57974 features from the two complex structures. By changing some of the parameters this number can be easily modified.

Statistical modelling on a data matrix with a size of 11905 by 57974 entries based on the 11905 corresponding phenotypic values was solved by applying a cascade of information theoretic principles.

The aim is to obtain a smaller number of relevant features to understand the mechanism of action for resistance. For N=28987 features there exist $2^N=9 \cdot 10^{8725}$ possible feature sets for explaining the phenotype which could feasibly take years to calculate.

The first stage of the statistical modelling comprised selecting the 1000 features with the highest information content $H_{SE}$(feature). Although 1000 features were selected in this example, it will be envisaged that this number may be changed. Since this set may still contain a large number of correlated features, the correlations are removed by using the Jensen-Shannon divergency, which is a special form of the Kullback-Leibler distance, $D_{JS}(P, P')$, where P and P' are the statistical distributions for feature and feature'. The correlation analysis scales with $O(|features|^2)$. The O-Notation is a typical mathematical notation describing the asymptotic behavior of functions (Cormen, T. H.; Leiserson, C. E. & Rivest, R. L. *Introduction to Algorithms*, MIT—Press, 1998, ISBN 0-262-03141-8). This is why this step was used after removing features having no or less information.

The most diverse set of features covering the diverse mutation pattern space was identified, for subsequent use in model building.

Finally, a feature selection filter was used, specifically the information gain $I_G(P, pFC)$, for selecting the best 200 features for characterising the phenotype.

Since the applied feature selection process ranks only single features, the final feature set quality must be evaluated by building machine learning models. In the present example, robust linear regression, decision tree, and AdaBoost.M1 ensemble models were built to evaluate the final feature set quality. All the methods used are documented and available in the open-source Weka machine-learning library It is clear that all of these models used a proper hypothesis testing procedure called k-cross-validation.

Regression versus Classification Phenotypic Prediction Models

Tables 1 and 2 show the prediction accuracy for predicting the pFC values based on the diverse interaction energy features. These values show the mean for correctly predicted classes for the 4-fold-cross-validated models. Additionally the standard error of mean is shown over the four folds.

TABLE 1

| Classification, 4-fold-CV (Darunavir) | Correct | Model complexity |
|---|---|---|
| Two classes (binary) (random 50%) C48 decision tree | 92.3 ± 0.3% | 126.5 ± 8.9 features |
| Two classes (binary) (random 50%) Adaboost.M1 ensemble of C48 trees | 92.8 ± 0.2% | ensemble model |
| Three classes (random 33%) | 77.0 ± 0.2% | 242.8 ± 31.73 features |

The decision tree models are not shown because they require an interactive browsing utility.

TABLE 2

| Regression, 4-fold-CV (Darunavir) | Correct | Model complexity |
|---|---|---|
| Robust linear regression | 92.3 ± 0.3% | 126.5 ± 8.9 features |

Since any model is biased to the data set used and the diversity selection might return different feature sets, it is important to create a statistical interpretation for the feature relevance. The prediction used therefore a four fold cross-validation, so four prediction models ranking features differently were obtained. Parts of those linear models are shown in Table 3 (CV-fold-1), Table 4 (CV-fold-2), Table 5 (CV-fold-3), and Table 6 (CV-fold-4).

The feature names contain information about the following parameters in the following order:

PartnerMolecule, ApoStructure, HomologyModelOptimization, ResidueNumber, InteractionPartnerI, InteractionPartnerII, AtomsUsed, EnergyTermUsed Where the parameter values can be:
PartnerMolecule={TMC114,APV}
ApoStructure={NOLIG,LIG}
HomologyModelOptimization={SDCH optimization only, ALL atom optimization}
ResidueNumber={1, 2, . . . , 99}
InteractionPartnerI={(chain)A,(chain)B,L(igand),W(ater)}
InteractionPartnerII={AB,BA,LA,LB,WA,WB}
AtomsUsed={SC sidechain,BB backbone, FULL residue}
EnergyTermUsed={VDW vanDerWaals, ELE electrostatic, ALL electronic terms}

TABLE 3

Linear contributions and features for fold number one. Robust linear regression for Darunavir model using diversity feature set of interaction energies.

| Factor in linear model | Structural Features |
|---|---|
| 1.32 | TMC114.NOLIG.SDCH.10.A.AB.INTE.SC.VDW + |
| −1.2514 | TMC114.LIG.SDCH.10.A.AB.INTE.SC.VDW + |
| 1.0899 | TMC114.LIG.ALL.47.B.B.INTE.FULL.ELE + |
| −1.0687 | TMC114.NOLIG.ALL.47.B.B.INTE.FULL.ELE + |
| 0.9425 | TMC114.LIG.ALL.84.B.BA.INTE.BB.ELE + |
| 0.8142 | TMC114.NOLIG.SDCH.75.B.BA.INTE.BB.VDW + |
| −0.8084 | TMC114.LIG.SDCH.74.A.LA.INTE.BB.ELE + |
| 0.7653 | TMC114.LIG.SDCH.74.A.LA.INTE.BB.ALL + |
| −0.7182 | TMC114.LIG.ALL.57.A.LA.INTE.BB.VDW + |
| 0.7124 | TMC114.LIG.ALL.57.A.LA.INTE.FULL.VDW + |
| −0.624 | TMC114.NOLIG.ALL.84.B.BA.INTE.BB.ELE + |
| −0.5918 | TMC114.LIG.SDCH.59.A.AB.INTE.BB.ALL + |
| −0.5887 | TMC114.LIG.ALL.44.B.BA.INTE.BB.VDW + |
| 0.5802 | TMC114.LIG.SDCH.59.A.AB.INTE.BB.ELE + |
| 0.5582 | TMC114.LIG.ALL.44.B.BA.INTE.FULL.VDW + |
| −0.5027 | TMC114.LIG.ALL.84.B.BA.INTE.BB.ALL + |
| −0.4916 | TMC114.LIG.SDCH.75.B.BA.INTE.BB.VDW + |
| −0.4395 | TMC114.LIG.ALL.84.B.BA.INTE.FULL.ELE + |
| 0.4393 | TMC114.NOLIG.ALL.84.B.BA.INTE.FULL.ELE + |
| 0.4275 | TMC114.NOLIG.ALL.84.A.WA.INTE.BB.ALL + |
| −0.3544 | TMC114.NOLIG.ALL.84.A.WA.INTE.BB.ELE + |
| . . . | . . . |
| 145 | features |

TABLE 4

Linear contributions and features for fold number two. Robust linear regression for Darunavir model using diversity feature set of interaction energies.

| Factor in linear model | Structural Features |
|---|---|
| −1.3554 | TMC114.LIG.ALL.44.B.BA.INTE.BB.VDW + |
| 1.3504 | TMC114.LIG.ALL.44.B.BA.INTE.FULL.VDW + |
| 1.3075 | TMC114.NOLIG.SDCH.84.A.AB.INTE.SC.VDW + |
| 1.2731 | TMC114.NOLIG.SDCH.84.A.WA.INTE.BB.ALL + |
| 1.1929 | TMC114.NOLIG.SDCH.47.A.A.INTE.FULL.ELE + |
| 1.1912 | TMC114.LIG.ALL.47.B.B.INTE.FULL.ELE + |
| −1.1669 | TMC114.NOLIG.ALL.47.B.B.INTE.FULL.ELE + |
| −1.1567 | TMC114.LIG.SDCH.47.A.A.INTE.FULL.ELE + |
| −1.1257 | TMC114.LIG.SDCH.44.B.BA.INTE.BB.VDW + |
| 1.1252 | TMC114.LIG.SDCH.47.B.B.INTE.FULL.ELE + |
| −1.1057 | TMC114.NOLIG.SDCH.84.A.WA.INTE.BB.ELE + |

TABLE 4-continued

Linear contributions and features for fold number two. Robust linear regression for Darunavir model using diversity feature set of interaction energies.

| Factor in linear model | Structural Features |
|---|---|
| −1.0877 | TMC114.NOLIG.SDCH.47.B.B.INTE.FULL.ELE + |
| 1.0628 | TMC114.LIG.SDCH.44.B.BA.INTE.FULL.VDW + |
| −0.9705 | TMC114.NOLIG.SDCH.84.A.AB.INTE.FULL.VDW + |
| 0.8857 | TMC114.LIG.ALL.84.A.WA.INTE.BB.ALL + |
| −0.8633 | TMC114.LIG.SDCH.51.A.A.INTE.FULL.ELE + |
| 0.8499 | TMC114.NOLIG.SDCH.51.A.A.INTE.FULL.ELE + |
| 0.8266 | TMC114.LIG.ALL.84.B.BA.INTE.BB.ELE + |
| −0.7508 | TMC114.LIG.ALL.84.B.BA.INTE.BB.ALL + |
| −0.731 | TMC114.NOLIG.ALL.84.B.BA.INTE.BB.ELE + |
| 0.7122 | TMC114.NOLIG.ALL.84.B.BA.INTE.BB.ALL + |
| . . . | . . . |
| 151 | features |

TABLE 5

Linear contributions and features for fold number three. Robust linear regression for Darunavir model using diversity feature set of interaction energies.

| Factor in linear models | Structural features |
|---|---|
| −1.6302 | TMC114.NOLIG.SDCH.84.B.BA.INTE.BB.ELE + |
| 1.5111 | TMC114.NOLIG.ALL.51.B.B.SASA + |
| −1.4814 | TMC114.LIG.ALL.51.B.B.SASA + |
| 1.3074 | TMC114.NOLIG.SDCH.84.B.BA.INTE.BB.ALL + |
| 1.2388 | TMC114.LIG.SDCH.84.B.BA.INTE.BB.ELE + |
| 1.2134 | TMC114.LIG.ALL.44.B.BA.INTE.FULL.VDW + |
| −1.1797 | TMC114.LIG.ALL.44.B.BA.INTE.BB.VDW + |
| −0.8745 | TMC114.LIG.SDCH.84.B.BA.INTE.BB.ALL + |
| −0.6614 | TMC114.LIG.SDCH.44.B.BA.INTE.BB.VDW + |
| 0.6536 | TMC114.LIG.SDCH.47.B.B.INTE.FULL.ELE + |
| 0.6308 | TMC114.NOLIG.SDCH.47.A.A.INTE.FULL.ELE + |
| 0.6229 | TMC114.LIG.SDCH.44.B.BA.INTE.FULL.VDW + |
| −0.6202 | TMC114.NOLIG.SDCH.47.B.B.INTE.FULL.ELE + |
| −0.6183 | TMC114.LIG.ALL.82.B.LB.INTE.FULL.ALL + |
| 0.6143 | TMC114.LIG.ALL.82.B.LB.INTE.FULL.VDW + |
| −0.5995 | TMC114.LIG.SDCH.47.A.A.INTE.FULL.ELE + |
| −0.5615 | TMC114.LIG.SDCH.86.A.A.INTE.FULL.VDW + |
| 0.551 | TMC114.LIG.ALL.47.B.B.INTE.FULL.ELE + |
| −0.5497 | TMC114.NOLIG.ALL.90.B.BA.INTE.SC.ELE + |
| 0.5419 | TMC114.NOLIG.SDCH.86.A.A.INTE.FULL.VDW + |
| −0.5116 | TMC114.NOLIG.ALL.47.B.B.INTE.FULL.ELE + |
| . . . | . . . |
| 145 | features |

TABLE 6

Linear contributions and features for fold number four. Robust linear regression for Darunavir model using diversity feature set of interaction energies.

| Factor in linear model | Structural Features |
|---|---|
| 1.9079 | TMC114.LIG.ALL.59.A.AB.INTE.BB.ELE + |
| −1.899 | TMC114.LIG.ALL.59.A.AB.INTE.BB.ALL + |
| −1.5271 | TMC114.LIG.SDCH.90.B.BA.INTE.FULL.VDW + |
| 1.5094 | TMC114.LIG.SDCH.90.B.BA.INTE.SC.VDW + |
| −1.4205 | TMC114.NOLIG.ALL.84.A.WA.INTE.BB.ELE + |
| 1.1659 | TMC114.NOLIG.ALL.84.A.WA.INTE.BB.ALL + |
| −1.1638 | TMC114.LIG.ALL.54.A.LA.INTE.FULL.VDW + |
| 1.1543 | TMC114.LIG.ALL.54.A.LA.INTE.SC.VDW + |
| 1.128 | TMC114.LIG.SDCH.51.A.A.INTE.FULL.ELE + |
| −1.1169 | TMC114.NOLIG.SDCH.51.A.A.INTE.FULL.ELE + |
| 0.9636 | TMC114.NOLIG.SDCH.47.A.A.INTE.FULL.ELE + |
| −0.947 | TMC114.LIG.SDCH.47.A.A.INTE.FULL.ELE + |
| −0.8497 | TMC114.LIG.ALL.44.B.BA.INTE.BB.VDW + |
| 0.8056 | TMC114.LIG.ALL.44.B.BA.INTE.FULL.VDW + |
| 0.7661 | TMC114.LIG.ALL.47.B.B.INTE.FULL.ELE + |
| −0.7465 | TMC114.NOLIG.ALL.47.B.B.INTE.FULL.ELE + |
| 0.6215 | TMC114.LIG.SDCH.84.B.BA.INTE.BB.ALL + |
| 0.621 | TMC114.NOLIG.ALL.51.A.A.INTE.FULL.ELE + |
| −0.5902 | TMC114.LIG.ALL.51.A.A.INTE.FULL.ELE + |
| −0.5608 | TMC114.LIG.SDCH.84.B.BA.INTE.BB.ELE + |
| 0.481 | TMC114.LIG.ALL.82.B.LB.INTE.FULL.VDW + |
| . . . | . . . |
| 162 | features |

Based on these cross-validated feature rankings, the relevance of the features might be investigated further due to their occurrence in the models. The underlying idea is that only relevant features are selected for the models, so only those features having a high relevance for understanding protein and drug resistance are selected. A statistical interpretation of feature groups was then calculated. Groups with a higher percentage are more relevant than those groups with a lower occurrence. Again, since it is not possible to evaluate all possible feature set combination, a statistical interpretation of the features sets finally used was created. A statistical analysis of the parameters and interaction energy groups for all selected features of the 4-fold cross-validated linear model for Darunavir is shown in Table 7 below.

TABLE 7

| Parameter or feature group | Occurrence over all selected features of CV-linear regression models | Description |
|---|---|---|
| Partner molecule = No | 40.83% | protein complex without partner molecule for interaction energy calculation |
| Partner molecule = Yes | 59.17% | protein complex without partner molecule for interaction energy calculation |
| SDCH | 57.50% | homology model generation uses side-chain optimization, only |
| ALL | 42.50% | homology model generation uses side-chain and backbone optimization |
| A | 42.67% | interactions with protein chain a |
| B | 57.33% | interactions with protein chain b |
| FULL | 40.33% | interactions with full residues |
| SC | 25.83% | interactions with side chain of residue |
| BB | 30.83% | interactions with backbone of residue |
| AB + BA | 41.00% | Interactions with protein chains a and b |
| WA | 16.00% | Interactions of protein chain a with the structural water |
| WB | 9.50% | Interactions of protein chain b with the structural water |
| LA | 10.50% | Interactions of chain a with the partner molecule (here Darunavir) |
| LB | 9.17% | Interactions of chain b with the partner molecules (here Darunavir) |
| ALL | 66.00% | Full energetic interactions |
| ELE | 25.17% | Electrostatic interactions |
| VDW | 48.83% | Van der Waals interactions |
| SASA | 3.00% | Residue surface features |

For example it can be seen that 57.33% of the relevant features have interactions with the protein chain B, and only 42.67% have interactions with chain A. Another interesting group describes the way the homology models are generated. There are two possible options, one uses the side chains optimization, only (parameter=SDCH protein atoms) and the other allows also a backbone optimization (parameter=ALL protein atoms). It can be seen that the side-chain optimization leads to features selected more often. This allows two conclusions to be drawn: Firstly that the backbone should not be varied and secondly that the actual homology modelling procedure should be adapted, e.g. by changing some homology modelling parameters like optimization cycles, optimization constraints, etc.

If the residue occurrence in the final models is considered then a structural conclusion from the feature selection after the model validation can be drawn as is shown in Table 8. The residues 84, 47, 44 and 51 occur in 73.8% of all the models. This is interesting taking into consideration that the model complexity for the cross-validated linear models is 126.5±8.9. In other words only four residues contribute to 73.8% of all the features selected.

TABLE 8

| residue | Occurrence |
|---------|------------|
| 84 | 28.57% |
| 47 | 21.43% |
| 44 | 14.29% |
| 51 | 9.52% |
| 59 | 4.76% |
| 82 | 3.57% |
| 90 | 3.57% |
| 10 | 2.38% |
| 54 | 2.38% |
| 57 | 2.38% |
| 74 | 2.38% |
| 75 | 2.38% |
| 86 | 2.38% |

Correlation Analysis of One Feature against All Available Features

As discussed above structural and mechanistic conclusions cannot be drawn by calcuating all possible combinatorial feature sets, since the complexity of this problem is too high. Such a problem is described as "NP complete" in computer science terminology. The presented tractable solution was to reduce the calculated features for those large data sets by using a cascade of information theoretic principles. This approach guarantees that relevant features are obtained, but it cannot guarantee that all relevant features are obtained. Even where cross-validation and stochastic sampling is applied there is still the possibility that some information will be missed.

In order to avoid this, all correlated features were calculated against a small identified relevant feature set to identify also other features relevant for a particular structural/mechanistic resistance phenomenon of interest.

The relevance can then be inspected using their calculated information content (Shannon entropy) and their Jensen-Shannon divergence. In addition, the visual correlation/divergence profiles can be inspected for all available feature combinations. FIG. 3 shows a selection for some complex interaction energies for residue 84. It must be noted that there are more than several hundred thousand interactions for residue 84, since the interactions are split into several interaction groups, like backbone, sidechain and full residue interactions, and many more.

Difference in Interactions of Mutated Residues with the Complex—with and without Partner Molecule The residue-complex interaction energy distributions in FIGS. 4 and 5 are without a bound partner molecule after the homolgy model generation. In contrast to that, the FIGS. 6 and 7 show the residue-complex energy distributions with bound partner molecule.

In both cases it can be seen that there is a huge difference in the interactions between protein chain A and protein chain B. This is an interesting effect, since the HIV protease is a homodimer, but the interactions are asymmetric. FIG. 8 shows the pair-wise residue-complex energy distribution with bound partner molecule which allows the identification of further clusters discriminating resistant from susceptible genotypes base don both protein chains A and B at the same time.

It can be seen that the mutation at residue 84 from an Ile to Val discriminates very well between highly resistant and susceptible mutants strain for Amprenavir. The definitions of highly resistant and susceptible value classes are illustrated in FIG. 2 wherein the bars of medium grey colour are highly resistant mutants, the bars of darkest grey colour are resistant mutants and the bars of lightest grey colour are susceptible mutants.

3D Mutation Pattern Diversity and 3D Partner Molecule Diversity

Following 3D model generation for each mutant pattern the models were stored in a database. A quick view on the modelled protein complex diversity was obtained by executing a k-Means clustering on the 3D coordinates for all structures and picking then the cluster centres. FIG. 9 shows an example for thirteen 3D models of this clustered diversity set. It must be noted that this 3D based atom diversity is already significantly different from a sequence mutation pattern diversity, since the energy minimized models allow different salvation models and residue movement constraints based on the given model building parameters H.

The protein, the partner molecule and a water molecule might be treated differently during the model generation. In the present example the water and the partner molecule have been allowed to move during the refinement process to represent a more realistic induced fit behaviour. The results are shown in FIG. 10.

Information Content and Complex Interaction Energy Difference

Another visualization mode for observing the uncertainty or non-conservation for residues in the generated 3D mutation structures is $H_{SE}$(feature)·[min(feature)·max(feature)]. This visualization can be applied on every interaction energy level and holistic splitting applied to the interaction energies. The same can be also done for the AAIndices, since they are just part of the feature vector. The kind of features used for this visualization depends on the user preference and in FIG. 11 and FIG. 12 the features calculating the full interaction energy of one residue against the full protein, partner molecule, and water molecule were used. It can be seen that the overall extremes are lower for Amprenavir, which suggests an averaged and more mobile partner molecule in the active site of the protein.

It must be noted that the grayscale-coding was only applied to the reference protein complex, but not to the diversity cluster or other generated protein complexes.

The invention claimed is:

1. A method of predicting the individual contribution of a mutated residue or set of mutated residues in a protein to the phenotype conferred by that mutated protein, said method comprising the steps of:
  (a) generating a 3D model of a complex of a partner molecule bound to said mutated protein by comparison with a 3D model of a complex of the same partner molecule bound to at least one first reference protein;
  (b) calculating the contribution of the mutated residue to the phenotype conferred by the mutated protein by quantifying the interaction energy between at least two of either (i) the protein and the partner molecule, (ii) the individual protein chains and the partner molecule, (iii) the individual protein residues and the partner molecule, (iv) the protein and the mutated residue, and (v) the individual protein chain(s) and the mutated residue;
  (c) comparing all or a subset of the contributions calculated in step (b) with the equivalent contribution in the at least one first reference protein complex by carrying out a cascade of dimensionality reduction steps that comprise calculating the Shannon entropy, calculating the Jensen-Shannon divergency, and calculating the information gain; and
  (d) predicting the phenotype conferred by the mutated protein from the difference in said contributions.

2. A method according to claim 1, wherein the interaction energies of step (b) are calculated by an atom-based or residue-based force-field technique.

3. A method according to claim 1 or 2, wherein step (b) includes calculating further 3D model dependent residue-specific descriptors for all residues in the mutated protein.

4. A method according to claim 1, wherein step (b) includes calculating further 3D model independent residue-specific descriptors for all residues.

5. A method according to claim 1, wherein the complexes of step (a) further comprise bound solvent molecule(s).

6. A method according to claim 5, wherein in step (b), the interaction energy between the protein and partner molecule at the level of (vi) bound solvent molecule-protein, (vii) bound solvent molecule-chain, and (viii) bound solvent molecule-residue is additionally quantified.

7. A method according to claim 1, wherein in step (a) the 3D model of the complex of the mutated protein is generated from a dataset comprising a list of genotypes and connected phenotypes.

8. A method according to claim 1, wherein after step (b) and before step (c), a further step of calculating the solvent accessible areas of the complex, protein, residue and partner molecule is included.

9. A method according to claim 1 wherein in step (b), the sequence of the protein is mapped to a physicochemical feature vector using amino acid similarity matrices and amino acid indices from the AA Index database.

10. A method according to claim 1, wherein the at least one first reference protein is the wild type protein.

11. A method according to claim 1, wherein the protein is a dimer.

12. A method according to claim 1, wherein the partner molecule is a drug and in step (d), the drug resistance phenotype conferred by the mutated protein is predicted.

13. A method according to claim 12, wherein the connected phenotype is the ratio of the log fold change (pFC) of the mutated genotype versus the drug resistance of the genotype of the at least one first reference protein.

14. A method according to claim 12, wherein in step (b), the contribution of the mutated residue to the log fold change (pFC) of the protein is calculated.

15. A method according to claim 12, wherein the cascade of dimensionality reduction steps is used to determine the most meaningful features for predicting the fold change (pFC) and the features identified are used to assign a quantitative resistance profile to areas of the drug, complex, protein, chain and/or residue.

16. A method according to claim 12, wherein the protein is an HIV 5 protease.

17. A method according to claim 1, wherein the protein is a receptor and the partner molecule is a small molecule or inhibitor for the receptor.

18. A method according to claim 1, wherein the steps (a) to (c) are repeated with a number of different partner molecules.

19. A diagnostic method for optimising a drug therapy in a patient, comprising performing a method according to any one of the preceding claims for each drug or combination of drugs being considered to obtain a series of drug resistance phenotypes and therefore assess the effect of the drug or combination of drugs on the resistance exhibited by the pathogen with which the patient is infected and selecting the drug or drug combination for which the pathogen is predicted to have the lowest resistance.

20. A computer apparatus or computer based system adapted to perform the method of claim 1.

21. A computer program product for use in conjunction with a computer, said computer comprising a computer readable storage medium and a computer program mechanism embedded therein, the computer program mechanism comprising a module that is configured so that upon receiving a request to predict the individual contribution of a mutated residue or a set of mutated residues in a protein to the drug resistance phenotype conferred by that protein, it performs a method according to claim 1.

22. A database containing information relating to the predicted individual contribution of a mutated residue or a set of mutated residues in a protein to the drug resistance phenotype conferred by that protein, said database being generated by performing a method as defined in claim 1.

* * * * *

SEQUENCE LISTING

```
<160> NUMBER OF SEQ ID NOS: 1

<210> SEQ ID NO 1
<211> LENGTH: 99
<212> TYPE: PRT
<213> ORGANISM: Human immunodeficiency virus type 1

<400> SEQUENCE: 1

Pro Gln Val Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Ser Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe
```